US008193145B2

(12) United States Patent
Burkin et al.

(10) Patent No.: US 8,193,145 B2
(45) Date of Patent: Jun. 5, 2012

(54) LAMININS, DERIVATIVES, AND COMPOSITIONS INCLUDING SAME AND METHODS FOR THEIR THERAPEUTIC USE

(75) Inventors: Dean J. Burkin, Sparks, NV (US); Jachinta E. Rooney, Reno, NV (US)

(73) Assignee: Board of Regents of the Nevada System of Higher Education, on Behalf of the University of Nevada, Reno, Reno, NV (US)

( * ) Notice: Subject to any disclaimer, the term of this patent is extended or adjusted under 35 U.S.C. 154(b) by 650 days.

(21) Appl. No.: 12/243,752

(22) Filed: Oct. 1, 2008

(65) Prior Publication Data

US 2009/0092587 A1    Apr. 9, 2009

Related U.S. Application Data

(60) Provisional application No. 60/998,320, filed on Oct. 9, 2007.

(51) Int. Cl.
*C07K 14/00* (2006.01)
(52) U.S. Cl. .......................................... 514/1; 530/350
(58) Field of Classification Search ....... 514/1; 530/350
See application file for complete search history.

(56) References Cited

U.S. PATENT DOCUMENTS

| | | | |
|---|---|---|---|
| 5,444,158 A | 8/1995 | Engvall et al. | |
| 6,294,356 B1 | 9/2001 | Jones et al. | |
| 6,566,074 B1 | 5/2003 | Goetinck | |
| 6,632,790 B1 * | 10/2003 | Yurchenco | 514/21.2 |
| 6,638,907 B1 | 10/2003 | Kortesmaa et al. | |
| 6,682,911 B1 | 1/2004 | Burgeson et al. | |
| 6,693,169 B1 | 2/2004 | Brunken et al. | |
| 6,858,395 B2 | 2/2005 | Kaufman | |
| 7,078,379 B2 | 7/2006 | Ruegg | |
| 2002/0111309 A1 | 8/2002 | Castillo et al. | |
| 2002/0192710 A1 | 12/2002 | Kaufman | |
| 2003/0013648 A1 | 1/2003 | Castillo et al. | |
| 2003/0224981 A1 | 12/2003 | Ruegg | |
| 2003/0232431 A1 | 12/2003 | Law | |
| 2004/0014665 A1 | 1/2004 | Boutaud | |
| 2005/0069985 A1 | 3/2005 | Kaufman | |
| 2005/0244384 A1 | 11/2005 | Law | |
| 2006/0014287 A1 | 1/2006 | Sherwood et al. | |
| 2006/0105455 A1 | 5/2006 | Guarino et al. | |
| 2007/0025972 A1 | 2/2007 | Rodriguez et al. | |
| 2007/0154552 A1 | 7/2007 | Siegal et al. | |
| 2009/0092587 A1 | 4/2009 | Burkin et al. | |

FOREIGN PATENT DOCUMENTS

WO    WO 97/38729    10/1997

OTHER PUBLICATIONS

Brown et al. 1999; Dystrophic phenotype induced in vitro by antibody blockade of muscle a-dystroglycan-laminin interaction. Journal of Cell Science 112: 209-216.*

Vachon et al. 1997; Integrins (a7b1) in muscle function and survival. Journal of Clinical Investigation. 100(7): 1870-1881.*
Allikian et al., "Genetic compensation for sarcoglycan loss by integrin α7β1 in muscle," *Journal of Cell Science*, vol. 117, pp. 3821-3830, 2004.
Chang, "Neuronal Ceroid Lipofuscinoses," 18pp., downloaded from the World Wide Web at http://www.emedicine.com/neuro/topic498.htm (marked May 21, 2007).
Chazalette et al., "α7B Integrin changes in mdx mouse muscles after L-arginine administration," *FEBS Letters*, vol. 579, pp. 1079-1084, 2005.
Colledge and Froehner, "To muster a cluster: Anchoring neurotransmitter receptors at synapses," *Proc. Natl. Acad. Sci. USA*, vol. 95, pp. 3341-3343, 1998.
Colognato et al., "Laminin Polymerization Induces a Receptor-Cytoskeleton Network," *Journal of Cell Biology*, vol. 145, No. 3, pp. 619-631, 1999.
Deconinck et al., "Functional protection of dystrophic mouse (*mdx*) muscles after adenovirus-mediated transfer of a dystrophin minigene," *Proc. Natl. Acad. Sci. USA*, vol. 93, pp. 3570-3574, 1996.
Dellorusso et al., "Functional correction of adult *mdx* mouse muscle using gutted adenoviral vectors expressing full-length dystrophin," *PNAS*, vol. 99, No. 20, pp. 12979-12984, 2002.
Dickson et al., "Co-localization and molecular association of dystrophin with laminin at the surface of mouse and human myotubes," *Journal of Cell Science*, vol. 103, pp. 1223-1233, 1992.
Duclos et al., "Progressive Muscular Dystrophy in α-Sarcoglycan-deficient Mice," *Journal of Cell Science*, vol. 142, No. 6, pp. 1461-1471, 1998.
Ervasti, "Costameres: the Achilles' Heel of Herculean Muscle," *Journal of Biological Chemistry*, vol. 278, No. 16, pp. 13591-13594, 2003.
Fu et al., "Protein stability in controlled-release systems," *Nature Biotechnology*, vol. 18, pp. 24-25, 2000.
Gawlik et al., "Laminin alpha1 chain reduces muscular dystrophy in laminin alpha2 chain deficient mice," *Hum. Mol. Genet.*, vol. 13, No. 16, pp. 1775-1784, 2004.
Gawlik et al., "Laminin alpha1 chain mediated reduction of laminin alpha2 chain deficient muscular dystrophy involves integrin alpha7beta1 and dystroglycan," *FEBS Letters*, vol. 580, No. 7, pp. 1759-1765, 2006.
Gawlik et al., "Laminin alpha1 chain improves laminin alpha2 chain deficient peripheral neuropathy," *Hum. Mol. Genet.*, vol. 15, No. 18, pp. 2690-2700, 2006.

(Continued)

*Primary Examiner* — Karen Cochrane Carlson
(74) *Attorney, Agent, or Firm* — Klarquist Sparkman, LLP

(57) ABSTRACT

In various embodiments, the present disclosure provides a method of treating a subject using laminin or a composition that includes laminin. In one embodiment, the method is used to enhance muscle regeneration, maintenance, or repair in a subject. In another embodiment, the method is used to promote wound healing. The method, in yet another embodiment, is used to prevent or reduce muscle damage or injury. In specific implementations of these methods, the laminin or composition that includes laminin is administered in a therapeutically effective amount. In some implementations, the laminin is a complete laminin protein. In other implementations, the laminin is a laminin fragment, a laminin derivative, or a laminin analogue.

22 Claims, 21 Drawing Sheets

OTHER PUBLICATIONS

Gullberg et al., "Laminins during muscle development and in muscular dystrophies," *Cell Mol. Life Sci.*, vol. 56, Nos. 5-6, pp. 442-460, 1999.

Guo et al., "Absence of α7 integrin in dystrophin-deficient mice causes a myopathy similar to Duchenne muscular dystrophy," *Hum. Mol. Genet.*, vol. 15, No. 6, pp. 989-998, 2006.

Hager et al., "Laminin {alpha}1 chain corrects male infertility causes by absence of laminin {alpha}2 chain," *Am. J. Path.*, vol. 167, No. 3, pp. 823-833, 2005.

Higuchi et al., "Abnormal Expression of Laminin Suggests Disturbance of Sarcolemma-Extracellular Matrix Interaction in Japanese Patients with Autosomal Recessive Muscular Dystrophy Deficient in Adhalin," *J. Clin. Invest.*, vol. 94, pp. 601-606, 1994.

Klietsch et al., "Dystrophin-Glycoprotein Complex and Laminin Colocalize to the Sarcolemma and Transverse Tubules of Cardiac Muscle," *Circulation Research*, vol. 72, No. 2, pp. 349-360, 1993.

Lowe, "Proteins to the Rescue?" 5 pp., downloaded from the World Wide Web at http://pipeline.corante.com/archives/2004/10/05/proteins_to_the_rescue (marked Sep. 27, 2007).

Milner and Kaufman, "α7β1 Integrin Does Not Alleviate Disease in a Mouse Model of Limb Girdle Muscular Dystrophy Type 2F," *Am. J. Path.*, vol. 170, No. 2, pp. 609-619, 2007.

Mort, "Multiple modes of drug delivery," *Modern Drug Discovery*, vol. 3, No. 3, pp. 30-32, 34, 2000.

Murthy et al., "A macromolecular delivery vehicle for protein-based vaccines: Acid-degradable protein-loaded microgels," *PNAS*, vol. 100, No. 9, pp. 4995-5000, 2003.

Nystrom et al., "Extraocular muscle is spared upon complete laminin alpha2 chain deficiency: comparative expression of laminin and integrin isoforms," *Matrix Biol.*, vol. 25, No. 6, pp. 382-385, 2006.

Ocalan et al., "Laminin Alters Cell Shape and Stimulates Motility and Proliferation of Murine Skeletal Myoblasts," *Developmental Biology*, vol. 125, pp. 158-167, 1988.

Orr-Urtreger et al., "Mice Deficient in the α7 Neuronal Nicotinic Acetylcholine Receptor Lack α-Bungarotoxin Binding Sites and Hippocampal Fast Nicotinic Currents," *Journal of Neuroscience*, vol. 17, No. 23, pp. 9165-9171, 1997.

Rooney et al., "Sever muscular dystrophy in mice that lack dystrophin and a α7 integrin," *Journal of Cell Science*, vol. 119, pp. 2185-2195, 2006.

Samarel, "Costameres, focal adhesions, and cardiomyocyte mechanotransductions," *Am. J. Physiol. Heart Circ. Physiol.*, vol. 289, pp. H2291-H2301, 2005.

Sher et al., "A Rostrocaudal Muscular Dystrophy Caused by a Defect in Choline Kinase Beta, the First Enzyme in Phosphatidylcholine Biosynthesis," *Journal of Biological Chemistry*, vol. 281, No. 8, pp. 4938-4948, 2006.

Sorokin et al., "Laminin alpha4 and integrin alpha6 are Upregulated in Regenerating dy/dy Skeletal Muscle: Comparative Expression of Laminin and Integrin Isoforms in Muscles Regenerating after Crush Injury," *Experimental Cell Research*, vol. 256, pp. 500-514, 2000.

Straub et al., "Molecular Pathogenesis of Muscle Degeneration in the δ-Sarcoglycan-Deficient Hamster," *American Journal of Pathology*, vol. 153, No. 5, pp. 1623-1630, 1998.

Uziyel et al., "Influence of laminin-2 on Schwann cell-axon interactions," *Glia.*, vol. 32, No. 2, pp. 109-121, 2000.

Vachon et al., "Merosin and Laminin in Myogenesis; Specific Requirement for Merosin in Myotube Stability and Survival," *Journal of Cell Biology*, vol. 134, No. 6, pp. 1483-1497, 1996.

Wang et al., "Cardiomyopathy Associated with Microcirculation Dysfunction in Laminin α4 Chain-deficient Mice," *Journal of Biological Chemistry*, vol. 281, No. 1, pp. 213-220, 2006.

Wang et al., "Binding of Injected Laminin to Developing Kidney Glomerular Mesangial Matrices and Basement Membranes in Vivo," *Journal of Histochemistry & Cytochemistry*, vol. 46, No. 3, pp. 291-300, 1998.

Yurchenco et al., "Loss of basement membrane, receptor and cytoskeletal lattices in a laminin-deficient muscular dystrophy," *Journal of Cell Science*, vol. 117, pp. 735-742, 2004.

Zhu et al., "Stabilization of proteins encapsulated in injectable poly (lactide-*co*-clycolide)," *Nature Biotechnology*, vol. 18, pp. 52-57, 2000.

Campbell Lab, "Molecular Studies of Muscular Dystrophy," 4 pp., downloaded from the World Wide Web at http://physiology.uiowa.edu/Campbell/Research/Areas/researchareas (marked Sep. 24, 2007).

Wikipedia, "Laminin," 2 pp., downloaded from the World Wide Web at http://en.wikipedia.org/w/index/php?title=Laminin (marked May 16, 2007).

Wikipedia, "Glycoprotein," 3 pp., downloaded from the World Wide Web at http://en.wikipedia.org/w/index.php?title=Glycoprotein (marked May 16, 2007).

Wikipedia, "Muscular Dystrophy," 7 pp., downloaded from the World Wide Web at http://en.wikipedia.org/w/index.php?title=Muscular_Dystrophy (marked May 16, 2007).

Wikipedia, "Myogenesis," 1 p., downloaded from the World Wide Web at http://en.wikipedia.org/wiki/Myogenesis (marked May 21, 2007).

Wikipedia, "Cyclophosphamide," 3 pp., downloaded from the World Wide Web at http://en.wikipedia.org/w/index.php?title=Cyclophosphamide (marked May 21, 2007).

Wikipedia, "MyoD," 2 pp., downloaded from the World Wide Web at http://en.wikipedia.org/w/index.php?title=MyoD (marked May 21, 2007).

Wikipedia, "Pax genes," 4 pp., downloaded from the World Wide Web at http://en.wikipedia.org/w/index.php?title=Pax_genes (marked May 21, 2007).

Wikipedia, "Bromodeoxyuridine," 1 p., downloaded from the World Wide Web at http://en.wikipedia.org/w/index.php?title=Bromodeoxyuridine (marked May 21, 2007).

Wikipedia, "Myosin," 5 pp., downloaded from the World Wide Web at http://en.wikipedia.org/w/index.php=title?Myosin (marked May 21, 2007).

Wikipedia, "Neuronal ceroid lipofuscinosis," 6 pp., downloaded from the World Wide Web at http://en.wikipedia.org/w/index.php?title=Neuronal_ceroid_lipofuscinosis (marked May 21, 2007).

Wikipedia, "Agrin," 2 pp., downloaded from the World Wide Web at http://en.wikipedia.org/w/index.php?title=Agrin (marked Sep. 19, 2007).

Wikipedia, "Proteoglycan," 2 pp., downloaded from the World Wide Web at http://en.wikipedia.org/w/index.php?title=Proteoglycan (marked Sep. 19, 2007).

Wikipedia, "Extracellular matrix," 5 pp., downloaded from the World Wide Web at http://en.wikipedia.org/w/index.php?title=Extracellular_matrix (marked Sep. 19, 2007).

Wikipedia, "Cell adhesion molecule," 3 pp., downloaded from the World Wide Web at http://en.wikipedia.org/w/index.php?title=Cell_adhesion_molecule (marked Sep. 19, 2007).

Wikipedia, "Integrin," 6 pp., downloaded from the World Wide Web at http://en.wikipedia.org/w/index.php?title=Integrin (marked Sep. 19, 2007).

Wikipedia, "Wound healing," 8 pp., downloaded from the World Wide Web at http://en.wikipedia.org/w/index.php?title=Wound_healing (marked Sep. 19, 2007).

Wikipedia, "Growth factor," 3 pp., downloaded from the World Wide at http://en.wikipedia.org/w/index.php?title=Growth_factor (marked Sep. 19, 2007).

Wikipedia, "Cytokine," 4 pp., downloaded from the World Wide Web at http://en.wikipedia.org/w/index.php?title=Cytokine (marked Sep. 19, 2007).

Wikipedia, "Protein domains," 17 pp., downloaded from the World Wide Web at http://en.wikipedia.org/w/index.php?title=Protein_domains (marked Sep. 19, 2007).

Wikipedia, "Satellite cells," 2 pp., downloaded from the World Wide Web at http://en.wikipedia.org/w/index.php?title=Satellite_cells (marked Sep. 19, 2007).

Wikipedia, "Mitosis," 4 pp., downloaded from the World Wide Web at http://en.wikipedia.org/w/index.php?title=Mitosis (marked Sep. 19, 2007).

Wikipedia, "Cell cycle," 6 pp., downloaded from the World Wide Web at http://en.wikipedia.org/w/index.php?title=Cell_cycle (marked Sep. 19, 2007).

Wikipedia, "Merosi," 1 p., downloaded from the World Wide Web at http://en.wikipedia.org/w/index.php?title=Merosin (marked Sep. 21, 2007).

Wikipedia, "Fibroblast," 3 pp., downloaded from the World Wide Web at http://en.wikipedia.org/w/index.php?title=Fibroblast (marked Sep. 24, 2007).

Wikipedia, "Basil lamina," 2 pp., downloaded from the World Wide Web at http://en.wikipedia.org/w/index.php?title=Basil_lamina (marked Sep. 24, 2007).

Wikipedia, "Route of administration," 3 pp., downloaded from the World Wide Web at http://en.wikipedia.org/w/index.php?title=Route_of_administration (marked Sep. 24, 2007).

Wikipedia, "Fibronectin," 2 pp., downloaded from the World Wide Web at http://en.wikipedia.org/w/index.php?title=Fibronectin (marked Sep. 24, 2007).

Wikipedia, "Dystrophin," 2 pp., downloaded from the World Wide Web at http://en.wikipedia.org/w/index.php?title=Dystroglycan (marked Sep. 24, 2007).

Wikipedia, "Dystroglycan," 2 pp., downloaded from the World Wide Web at http://en.wikipedia.org/w/index.php?title=Dystroglycan (marked Sep. 24, 2007).

Wikipedia, "Sarcomere," 3 pp., downloaded from the World Wide Web at http://en.wikipedia.org/w/index.php?title=Sarcomere (marked Sep. 24, 2007).

Wikipedia, "Sarcolemma," 1 p., downloaded from the World Wide Web at http://en.wikipedia.org/w/index.php?title=Sarcolemma (marked Sep. 24, 2007).

Wikipedia, "Myofibril," 2 pp., downloaded from the World Wide Web at http://en.wikipedia.org/w/index.php?title=Myofibril (marked Sep. 24, 2007).

Wikipedia, "Muscle fiber," 3 pp., downloaded from the World Wide Web at http:en.wikipedia.org/w/index.php?title=Muscle_fiber (marked Sep. 24, 2007).

Wikipedia, "Myoblast," 1 p., downloaded from the World Wide Web at http://en.wikipedia.org/w/index.php?title=Myoblast (marked Sep. 24, 2007).

Wikipedia, "Nestin (protein)," 3 pp., downloaded from the World Wide Web at http://en.wikipedia.org/w/index.php ?title=Nestin_%28protein (marked Sep. 2007).

Wikipedia, "Green fluorescent protein," 5 pp., downloaded from the World Wide Web at http://en.wikipedia.org/w/index.php?title=Green_fluorescent_protein (marked Sep. 25, 2007).

Wikipedia, "Utrophin," 2 pp., downloaded from the World Wide Web at http://en.wikipedia.org/w/index.php?title=Utrophin (marked Sep. 25, 2007).

Wikipedia, "Cadherin," 1 p., downloaded from the World Wide Web at http://en.wikipedia.org/w/index.php?title=Cadherin (marked Sep. 26, 2007).

Wikipedia, "Transcription factor," 8 pp., downloaded from the World Wide Web at http://en.wikipedia.org/w/index.php?title=Transcription_factor (marked Sep. 26, 2007).

Wikipedia, "Zygosity," 3 pp., downloaded from the World Wide Web at http://en.wikipedia.org/w/index.php?title=Zygosity (marked Oct. 2, 2007).

Extended European Search Report issued Dec. 6, 2011, by the European Patent Office for related European Patent Application No. EP 08 83 6948, 9 pp.

Hashimoto et al., "Development of alginate wound dressings linked with hybrid peptides derived from laminin and elastin," *Biomaterials*, vol. 25, No. 7-8, pp. 1407-1413, Mar. 1, 2004.

Jimenez-Mallebrera et al., "Congenital muscular dystrophy: molecular and cellular aspects," *CMLS Cellular and Molecular Life Sciences*, vol. 62, No. 7-8, Apr. 1, 2005.

Thornell et al., "Fibronectin and laminin related to myocardial damage and repair," *Journal of Molecular and Cellular Cardiology*, vol. 23, p. S13 (Abstract) Jul. 1, 1991.

Weber-Schuerholz et al., "Muscle regeneration possible mitogenic role of laminin and its proteolytic fragments," *European Journal of Cell Biology Supplement*, p. 42 (Abstract) Jan. 1, 1990.

* cited by examiner

C2C12

α7B

Cox-1

DMD

α7B

Cox-1

LAMININS, DERIVATIVES, AND COMPOSITIONS INCLUDING SAME AND METHODS FOR THEIR THERAPEUTIC USE

CROSS REFERENCE TO RELATED APPLICATION

This application claims the benefit of, and incorporates by reference, U.S. Provisional Patent Application No. 60/998,320, filed Oct. 9, 2007. This application incorporates by reference International Patent Application No. PCT/US08/78459, filed Oct. 1, 2008.

STATEMENT OF GOVERNMENT SUPPORT

This invention was made with United States Government support under grants from the National Institutes of Health (NIH), National Center for Research Resources, Grant Nos. NCRR P20 RR018751-01, P20 RR15581-04; National Institute of Arthritis and Musculoskeletal and Skin Diseases, Grant No. NIAMS R01AR053697-01; and National Institute of Neurological Disorders and Stroke, Grant No. NINDS R21NS058429-01. The United States Government has certain rights in the invention.

FIELD

The present disclosure relates to a method of providing therapeutic benefit to a subject by administering to the subject a laminin or a composition that includes laminin. In a particular embodiment, the present disclosure provides a method of enhancing muscle regeneration, such as to treat muscular dystrophy, in a subject by administering laminin or a laminin composition.

BACKGROUND

Adult skeletal muscle exhibits a remarkable ability to repair and regenerate after trauma or injury. The regenerative capacity of skeletal muscle is due to a reservoir of satellite cells located under the basal lamina and in close proximity to the myofiber sarcolemma. These cells remain quiescent in healthy uninjured muscle, but are rapidly activated in response to muscle damage, exercise, or disease.

Upon activation, satellite cells proliferate and differentiate down the myogenic pathway and are able to repair damaged muscle. Models suggest a subpopulation of satellite cells remain as stem cells to replace activated cells that have progressed down the myogenic lineage pathway. During the activation period, satellite cells express the transcription factors Pax3, Pax7, MyoD, myogenin, and MRF4 as they progress through a developmental program towards muscle repair.

Muscular dystrophy is a term used to refer to a group of genetic disorders that lead to progressive muscle weakness. Muscular dystrophy can result in skeletal muscle weakness and defects in skeletal muscle proteins, leading to a variety of impaired physiological functions. No satisfactory treatment of muscular dystrophy exists. Existing treatments typically focus on ameliorating the effects of the disease and improving the patient's quality of life, such as through physical therapy or through the provision of orthopedic devices.

Mutated genes associated with muscular dystrophy are responsible for encoding a number of proteins associated with the costameric protein network. Such proteins include laminin-2, collagen, dystroglycan, integrins, caveolin-3, ankyrin, dystrophin, $\alpha$-dystrobrevin, vinculin, plectin, BPAG1b, muscle LIM protein, desmin, actinin-associated LIM protein, $\alpha$-actin, titin, telethonin, cypher, myotilin, and the sarcoglycan/sarcospan complex.

The most common form of muscular dystrophy, Duchenne muscular dystrophy, is caused by a mutation in the gene responsible for production of dystrophin. Dystrophin is a protein involved in binding cells to the extracellular matrix, including the basement membrane. Congenital muscular dystrophies are caused by gene mutations affecting the production of other costameric proteins. For example, in populations of European descent, the most prevalent congenital muscular dystrophy is caused by a mutation resulting in a lack of $\alpha7\beta1$ integrin expression. Like dystrophin, $\alpha7\beta1$ integrin is involved in binding cells to the extracellular matrix.

To some extent, a defect in the gene encoding for one of dystrophin or $\alpha7\beta1$ integrin is often compensated for by enhanced expression of the other, or another costameric protein, such as utrophin (an analog of dystrophin). Dystrophin, $\alpha7\beta1$ integrin, and utrophin all serve as receptors for laminin, which serves as the link to the extracellular matrix. Defective production of laminin-2 itself gives rise to merosin-deficient congenital muscular dystrophy (MCMD) or congenital muscular dystrophy type 1A (MDC1A).

Laminin is a major component of the basement membrane. At least fifteen laminin protein trimers have been identified, each a heterotrimer including an $\alpha$, $\beta$, and $\gamma$ chain. Laminin is associated with a number of physiological functions, including cell attachment, gene expression, tyrosine phosphorylation of proteins, cell differentiation, as well as cell shape and movement. Laminin is known to bind to cell membranes through integrin receptors. In addition, laminin-2 binds to $\alpha$-dystroglycan as part of the dystrophin-glycoprotein complex.

The $\alpha7\beta1$ integrin is a major laminin receptor expressed in skeletal muscle. The $\alpha7\beta1$ integrin plays an important role in the development of neuromuscular and myotendinous junctions. In the adult, the $\alpha7\beta1$ integrin is concentrated at junctional sites and found in extrajunctional regions where it mediates the adhesion of the muscle fibers to the extracellular matrix. Mice that lack the $\alpha7$ chain develop muscular dystrophy that affects the myotendinous junctions. The absence of $\alpha7$ integrin results in defective matrix deposition at the myotendinous junction. Loss of the $\alpha7$ integrin in $\gamma$-sarcoglycan mice results in severe muscle pathology. Absence of the $\alpha7$ integrin in mdx mice also results in severe muscular dystrophy, confirming that the $\alpha7\beta1$ integrin serves as a major genetic modifier for Duchenne and other muscular dystrophies.

Mutations in the $\alpha7$ gene are responsible for muscular dystrophy in humans. A screen of 117 muscle biopsies from patients with undefined muscle disease revealed 3 which lacked the $\alpha7$ integrin chain and had reduced levels of $\beta1D$ integrin chain. These patients exhibit delayed developmental milestones and impaired mobility consistent with the role for the $\alpha7\beta1$ integrin in neuromuscular and myotendinous junction development and function.

Several lines of evidence suggest the $\alpha7$ integrin may be important for muscle regeneration. For example, during embryonic development, the $\alpha7\beta1$ integrin regulates myoblast migration to regions of myofiber formation. It has been found that MyoD (myogenic determination protein) transactivates $\alpha7$ integrin gene expression in vitro, which would increase $\alpha7$ integrin levels in activated satellite cells. Human, mouse and rat myoblast cell lines derived from satellite cells express high levels of $\alpha7$ integrin. Elevated $\alpha7$ integrin mRNA and protein are detected in the skeletal muscle of 5 week old mdx mice, which correlates with the period of maximum muscle degeneration and regeneration. In addition, the α7β1 integrin associates with muscle specific $α_1$-integrin binding protein (MIBP), which regulates laminin deposition in C2C12 myoblasts. Laminin provides an environment that supports myoblast migration and proliferation. Finally, enhanced expression of the α7 integrin in dystrophic skeletal muscle results in increased numbers of satellite cells.

To date, many efforts to cure or ameliorate muscular dystrophy involve enhancing expression of various components of the costameric network. However, these approaches, while showing some promise in vitro or in transgenic animals, typically do not demonstrate effective results in humans nor provide methods through which therapy could be accomplished in humans. Such routes of therapy are notoriously difficult to implement.

However, it is also well known that direct administration of proteins, particularly large proteins, is very difficult. For example, large size, high charge, short half life, poor stability, high immunogenicity, and poor membrane permeability can limit the bioavailability of administered proteins. In addition, depending on the route of administration, a subject's natural physiological processes can attack and degrade administered proteins. For example, although laminin is known to play a role in the extracellular matrix, it is a particularly large (typically >600 kD), highly charged molecule and consequently difficulties in its administration to patients would likely have been anticipated. Accordingly, efforts to date have focused on more sophisticated treatments, rather than direct administration of therapeutic substances.

SUMMARY

In various embodiments, the present disclosure provides a method of treating a subject with laminin or a composition that includes laminin. For example, some embodiments provide methods of improving muscular health, such as enhancing muscle regeneration, maintenance, or repair in a subject by administering to the subject an effective amount of laminin or a composition comprising laminin, including fragments, derivatives, or analogs thereof. In a specific example, the laminin is a complete laminin protein. In further examples, the laminin is selected from laminin-1, laminin-2, laminin-4, and combinations thereof. In further examples, the laminin or laminin composition includes a substance at least substantially homologous to laminin-1, laminin-2, or laminin-4. In yet further implementations, the laminin or laminin composition comprises a polypeptide at least substantially homologous to the laminin α1 chain.

In additional examples, the laminin or laminin composition consists of laminin-1, laminin-2, laminin-4, and combinations thereof. In further examples, the laminin or laminin composition consists of a substance at least substantially homologous to laminin-1, laminin-2, or laminin-4. In yet further implementations, the laminin or laminin composition consists of a polypeptide at least substantially homologous to the laminin α1 chain. In a specific example, the laminin or laminin composition does not include a laminin fragment, such as including only a complete laminin protein.

In yet another example, the laminin or laminin composition consists essentially of laminin-1, laminin-2, laminin-4, and combinations thereof. In further examples, the laminin or laminin composition consists essentially of a substance at least substantially homologous to laminin-1, laminin-2, or laminin-4. In yet further implementations, the laminin or laminin composition consists essentially of a polypeptide at least substantially homologous to the laminin α1 chain. In a specific example, the laminin or laminin composition does not include a laminin fragment, such as including essentially only a complete laminin protein.

Further implementations of the disclosed method include diagnosing the subject as having a condition treatable by administering laminin or a composition comprising laminin. In one example, the subject is diagnosed as suffering from muscular dystrophy, such as a congenital muscular dystrophy, Duchenne muscular dystrophy, or Limb-girdle muscular dystrophy. In further instances the condition is characterized by the failure of a subject, or the reduced ability of the subject, to express one or more proteins associated with the formation or maintenance of the extracellular matrix, such as impaired or non-production of a laminin, an integrin, dystrophin, utrophin, or dystroglycan.

In a specific embodiment, the present disclosure also provides a method for increasing muscle regeneration in a subject. For example, geriatric subjects, subjects suffering from muscle disorders, and subjects suffering from muscle injury, including activity induced muscle injury, such as injury caused by exercise, may benefit from this embodiment.

In yet further embodiments of the disclosed method, the laminin or laminin composition is administered in a preventative manner, such as to prevent or reduce muscular damage or injury (such as activity or exercise induced injury). For example, geriatric subjects, subjects prone to muscle damage, or subjects at risk for muscular injury, such as athletes, may be treated in order to eliminate or ameliorate muscular damage, injury, or disease.

Implementations of the present disclosure may also be used to promote wound healing. In some examples, a laminin or a composition comprising laminin is administered into or proximate to a wound. In further examples, the substance is administered systemically. Although the substance is typically applied after the wound occurs, the substance is applied prospectively in some examples.

In further embodiments, the method of the present disclosure includes administering the laminin or laminin composition with one or more additional pharmacological substances, such as a therapeutic agent. In some aspects, the additional therapeutic agent enhances the therapeutic effect of the laminin or laminin composition. In further aspects, the therapeutic agent provides independent therapeutic benefit for the condition being treated. In various examples, the additional therapeutic agent is a component of the extracellular matrix, such as an integrin, dystrophin, dystroglycan, utrophin, or a growth factor. In further examples, the therapeutic agent reduces or enhances expression of a substance that enhances the formation or maintenance of the extracellular matrix.

In some examples, the laminin or laminin composition is applied to a particular area of the subject to be treated. For example, the laminin or laminin composition may be injected into a particular area to be treated, such as a muscle. In further examples, the laminin or laminin composition is administered such that it is distributed to multiple areas of the subject, such as systemic administration or regional administration.

Laminin, or a composition comprising laminin, can be administered by any suitable method, such as topically, parenterally (such as intravenously or intraperitoneally), or orally. In a specific example, the laminin or laminin composition is administered systemically, such as through parenteral administration, such as stomach injection or peritoneal injection.

Although the disclosed methods generally have been described with respect to muscle regeneration, the disclosed methods also may be used to enhance repair or maintenance, or prevent damage to, other tissues and organs. For example, the methods of the present disclosure can be used to treat symptoms of muscular dystrophy stemming from effects to cells or tissue other than skeletal muscle, such as impaired or altered brain function, smooth muscles, or cardiac muscles.

There are additional features and advantages of the various embodiments of the present disclosure. They will become evident from the following disclosure.

In this regard, it is to be understood that this is a brief summary of the various embodiments described herein. Any given embodiment of the present disclosure need not provide all features noted above, nor must it solve all problems or address all issues in the prior art noted above.

DETAILED DESCRIPTION

Figure 1:
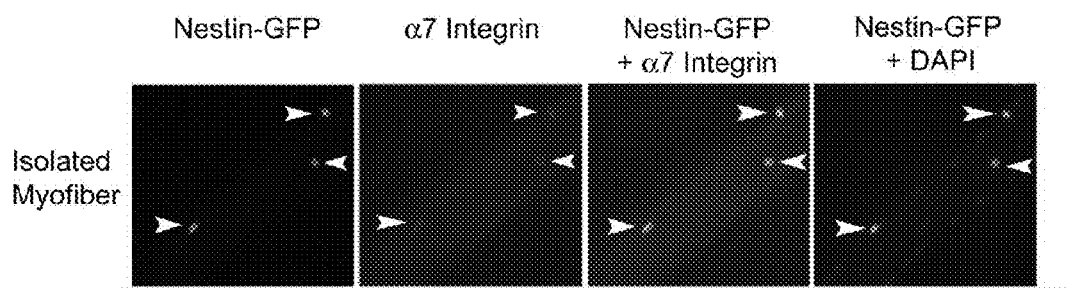
FIG. 1 is immunofluorescence images of myofibers isolated from nestin-GFP transgenic mice using an anti-α7 integrin monoclonal antibody.

Abbreviations
PBS—phosphate-buffered saline
LAM-111—laminin-1, which includes the chains α1β1γ1
NaCl—sodium chloride
NaOH—sodium hydroxide
HCl—hydrochloric acid
MCMD, MDC1A—merosin-deficient congenital muscular dystrophy
DMSO—dimethylsulfoxide
EDTA—ethylenediaminetetraacetic acid
eMyHC—embryonic myosin heavy chain
BrdU—bromodeoxyuridine
TA—tibialis anterior
H&E—hematoxylin and eosin
GFP—green fluorescent protein
WT—wild-type
EBD—Evan's blue dye
DMD—Duchenne muscular dystrophy
CLN—centrally located nuclei
nmol—nanomole
nM—nanomolar
MyoD—myogenic determination protein
MIBP—muscle specific $\alpha_1$-integrin binding protein
FACS—fluorescence activated sorting
FITC—fluorescein isothiocyanate
Pax7—paired box gene 7
Pax3—paired box gene 3
Cox-1—cyclooxygenase-1
MRF4—myogenic factor 6
Terms In order to facilitate an understanding of the embodiments presented, the following explanations are provided.

Unless otherwise explained, all technical and scientific terms used herein have the same meaning as commonly understood by one of ordinary skill in the art to which this disclosure belongs. In case of conflict, the present specification, including explanations of terms, will control. The singular terms "a," "an," and "the" include plural referents unless context clearly indicates otherwise. Similarly, the word "or" is intended to include "and" unless the context clearly indicates otherwise. The term "comprising" means "including;" hence, "comprising A or B" means including A or B, or including A and B. All numerical ranges given herein include all values, including end points (unless specifically excluded) and any and all intermediate ranges between the endpoints.

Although methods and materials similar or equivalent to those described herein can be used in the practice or testing of the present disclosure, suitable methods and materials are described herein. The disclosed materials, methods, and examples are illustrative only and not intended to be limiting.

"Muscle" refers to any myoblast, myocyte, myofiber, myotube or other structure composed of muscle cells. Muscles or myocytes can be skeletal, smooth, or cardiac. Muscle may also refer to, in particular implementations of the present disclosure, cells or other materials capable of forming myocytes, such as stem cells and satellite cells.

"Extracellular matrix" refers to the extracellular structure of a tissue or a layer thereof, including the arrangement, composition, and forms of one or more matrix components, such as proteins, including structural proteins such as collagen and elastin, proteins such as fibronectin and laminins, and proteoglycans. The matrix may comprise fibrillic collagen, having a network of fibers. In some examples, the extracellular matrix is connected to cells through the costameric protein network.

"Tissue" refers to an aggregate of cells, usually of a particular kind, together with their intercellular substance that form one of the structural materials of an animal and that in animals include connective tissue, epithelium, muscle tissue, and nerve tissue.

"Subject" refers to an organism, such as an animal, to whom treatments are administered. Subjects include mammals, such as humans, pigs, rats, cows, mice, dogs, cats, and primates.

"Laminin" refers to any of the family of glycoproteins that are typically involved in the formation and maintenance of extracellular matrices. Laminin is a heterotrimers formed from an α chain, β chain, and a γ chain. The various chains of a particular laminin can affect the properties of the molecule. In some aspects of the present disclosure, fragments, derivatives, or analogs of various laminins can be used, such as laminins having at least a portion at least substantially homologous to the laminin α1 chain.

"At least substantially homologous," as used in the present disclosure, refers to a degree of homology sufficient to produce at least a portion of the activity of a reference material in muscle regeneration, maintenance or repair, or wound healing. In some examples, materials are at least substantially homologous when they are at least about 95%, at least about 98%, or at least about 99% homologous to a reference material.

A "fragment," as used herein, refers to a portion of a substance, such as laminin. A fragment may be, in some examples, a particular domain or chain of a protein. For example, particular embodiments of the present disclosure involve administering a fragment of laminin-1 corresponding to at least a portion of (or all of) the laminin α1 chain. Fragments may be synthetic or may be derived from larger parent substances.

A "derivative," as used herein, refers to a form of a substance, such as a laminin or portion thereof, which has at least one functional group altered, added, or removed, compared with the parent compound.

"Functional group" refers to a radical, other than a hydrocarbon radical, that adds a physical or chemical property to a substance.

As used herein, an "analog" refers to a compound which is sufficiently homologous to a compound such that it has a similar functional activity for a desired purpose as the original compound. Analogs include polypeptides having one or more amino acid substitutions compared with a particular substance.

In some aspects, laminins may be administered as a mixture of laminins, including fragments, analogs, and derivatives thereof. Suitable methods for preparing analogs of laminin domains are disclosed in U.S. Pat. No. 6,933,280, incorporated by reference herein to the extent not inconsistent with this disclosure.

The laminin materials or compositions of the present disclosure may be delivered as discrete molecules or may be complexed with, or conjugated to, another substance. For example, the laminin may be combined with a carrier, such as to aid in delivery of the laminin to a site of interest or to increase physiological uptake or incorporation of the laminin.

In specific examples, the laminin administered includes or consists of laminin-1 (LAM-111), which includes the chains α1β1γ1. In further examples, the laminin administered includes or consists of laminin-2, which includes the chains α2β1γ1. In yet further examples, the laminin administered includes or consists of laminin-4, which includes the chains α2β2γ1.

Laminins may be obtained from any suitable source. For example, laminin-1 may be obtained from placental tissue or from Engelbreth-Holm-Swarm murine sarcoma. Suitable methods of isolating various laminins are disclosed in U.S. Pat. No. 5,444,158, incorporated by reference herein to the extent not inconsistent with the present disclosure.

"Biological source" refers to an organism, such as an animal, such as a mammal, or portion thereof, from which biological materials may be obtained. Examples of such materials include tissue samples, such as placental material or sarcoma; cells, such as satellite cells; extracellular material, including laminins or other components thereof; or other organic or inorganic material found in the organism.

"Improving muscular health" refers to an improvement in muscular health compared with a preexisting state or compared with a state which would occur in the absence of treatment. For example, improving muscular health may include enhancing muscle regeneration, maintenance, or repair. Improving muscular health may also include prospectively treating a subject to prevent or reduce muscular damage or injury.

"Regeneration" refers to the repair of cells or tissue, such as muscle cells or tissue (or organs) which includes muscle cells, following injury or damage to at least partially restore the muscle or tissue to a condition similar to which the cells or tissue existed before the injury or damage occurred. Regeneration also refers to facilitating repair of cells or tissue in a subject having a disease affecting such cells or tissue to eliminate or ameliorate the effects of the disease. In more specific examples, regeneration places the cells or tissue in the same condition or an improved physiological condition as before the injury or damage occurred or the condition which would exist in the absence of disease.

"Maintenance" of cells or tissue, such as muscle cells or tissue (or organs) which includes muscle cells, refers to maintaining the cells or tissue in at least substantially the same physiological condition, such as maintaining such condition even in the presence of stimulus which would normally cause damage, injury, or disease.

"Repair" of cells or tissue, such as muscle cells or tissue (or organs) which includes muscle cells, refers to the physiological process of healing damage to the cells or tissue following damage or other trauma.

"Administering" refers to providing one or more substances to a subject such that the subject may receive therapeutic benefit from the substance. The laminin, laminin composition, or other therapeutic substance are in general administered topically, nasally, intravenously, orally, intracranially, intramuscularly, parenterally or as implants, but even rectal or vaginal use is possible in principle. Laminin, or compositions thereof, also may be administered to a subject using a combination of these techniques.

Suitable solid or liquid pharmaceutical preparation forms are, for example, aerosols, (micro)capsules, creams, drops, drops or injectable solution in ampoule form, emulsions, granules, powders, suppositories, suspensions, syrups, tablets, coated tablets, and also preparations with protracted release of active compounds, in whose preparation excipients and additives and/or auxiliaries such as binders, coating agents, disintegrants, flavorings, lubricants, solubilizers, sweeteners, or swelling agents are customarily used as described above. The pharmaceutical compositions are suitable for use in a variety of drug delivery systems. For a brief review of various methods for drug delivery, see Langer, "New Methods of Drug Delivery," *Science* 249:1527-1533 (1990), incorporated by reference herein to the extent not inconsistent with the present disclosure.

The laminin, laminin compositions, or other therapeutic agents of the present disclosure can be formulated into therapeutically-active pharmaceutical compositions that can be administered to a subject parenterally or orally. Parenteral administration routes include, but are not limited to epidermal, intraarterial, intramuscular (IM and depot IM), intraperitoneal (IP), intravenous (IV), intrasternal injection or infusion techniques, intranasal (inhalation), intrathecal, injection into the stomach, subcutaneous injections (subcutaneous (SQ and depot SQ), transdermal, topical, and ophthalmic.

The laminin, laminin composition, or other therapeutic agent can be mixed or combined with a suitable pharmaceutically acceptable excipients to prepare pharmaceutical compositions. Pharmaceutically acceptable excipients include, but are not limited to, alumina, aluminum stearate, buffers (such as phosphates), glycine, ion exchangers (such as to help control release of charged substances), lecithin, partial glyceride mixtures of saturated vegetable fatty acids, potassium sorbate, serum proteins (such as human serum albumin), sorbic acid, water, salts or electrolytes such as cellulose-based substances, colloidal silica, disodium hydrogen phosphate, magnesium trisilicate, polyacrylates, polyalkylene glycols, such as polyethylene glycol, polyethylene-polyoxypropylene-block polymers, polyvinyl pyrrolidone, potassium hydrogen phosphate, protamine sulfate, group 1 halide salts such as sodium chloride, sodium carboxymethylcellulose, waxes, wool fat, and zinc salts, for example. Liposomal suspensions may also be suitable as pharmaceutically acceptable carriers.

Upon mixing or addition of the laminin, laminin composition, or other therapeutic agent, the resulting mixture may be a solid, solution, suspension, emulsion, or the like. These may be prepared according to methods known to those of ordinary skill in the art. The form of the resulting mixture depends upon a number of factors, including the intended mode of administration and the solubility of the agent in the selected carrier.

Pharmaceutical carriers suitable for administration of the laminin, laminin composition, or other therapeutic agent include any such carriers known to be suitable for the particular mode of administration. In addition, the laminin, laminin composition, or other therapeutic substance can also be mixed with other inactive or active materials that do not impair the desired action, or with materials that supplement the desired action, or have another action.

Methods for solubilizing may be used where the agents exhibit insufficient solubility in a carrier. Such methods are known and include, but are not limited to, dissolution in aqueous sodium bicarbonate, using cosolvents such as dimethylsulfoxide (DMSO), and using surfactants such as TWEEN® (ICI Americas, Inc., Wilmington, Del.).

The laminin, laminin composition, or other therapeutic agent can be prepared with carriers that protect them against rapid elimination from the body, such as coatings or time-release formulations. Such carriers include controlled release formulations, such as, but not limited to, microencapsulated delivery systems. The laminin, laminin composition, or other therapeutic agent is included in the pharmaceutically acceptable carrier in an amount sufficient to exert a therapeutically useful effect, typically in an amount to avoid undesired side effects, on the treated subject. The therapeutically effective concentration may be determined empirically by testing the compounds in known in vitro and in vivo model systems for the treated condition. For example, mouse models of muscular dystrophy may be used to determine effective amounts or concentrations that can then be translated to other subjects, such as humans, as known in the art.

Injectable solutions or suspensions can be formulated, using suitable non-toxic, parenterally-acceptable diluents or solvents, such as 1,3-butanediol, isotonic sodium chloride solution, mannitol, Ringer's solution, saline solution, or water; or suitable dispersing or wetting and suspending agents, such as sterile, bland, fixed oils, including synthetic mono- or diglycerides, and fatty acids, including oleic acid; a naturally occurring vegetable oil such as coconut oil, cottonseed oil, peanut oil, sesame oil, and the like; glycerine; polyethylene glycol; propylene glycol; or other synthetic solvent; antimicrobial agents such as benzyl alcohol and methyl parabens; antioxidants such as ascorbic acid and sodium bisulfite; buffers such as acetates, citrates, and phosphates; chelating agents such as ethylenediaminetetraacetic acid (EDTA); agents for the adjustment of tonicity such as sodium chloride and dextrose; and combinations thereof. Parenteral preparations can be enclosed in ampoules, disposable syringes, or multiple dose vials made of glass, plastic, or other suitable material. Buffers, preservatives, antioxidants, and the like can be incorporated as required. Where administered intravenously, suitable carriers include physiological saline, phosphate-buffered saline (PBS), and solutions containing thickening and solubilizing agents such as glucose, polyethylene glycol, polypropyleneglycol, and mixtures thereof. Liposomal suspensions, including tissue-targeted liposomes, may also be suitable as pharmaceutically acceptable carriers.

For topical application, the laminin, laminin composition, or other therapeutic agent may be made up into a cream, lotion, ointment, solution, or suspension in a suitable aqueous or non-aqueous carrier. Topical application can also be accomplished by transdermal patches or bandages which include the therapeutic substance. Additives can also be included, e.g., buffers such as sodium metabisulphite or disodium edetate; preservatives such as bactericidal and fungicidal agents, including phenyl mercuric acetate or nitrate, benzalkonium chloride, or chlorhexidine; and thickening agents, such as hypromellose.

If the laminin, laminin composition, or other therapeutic agent is administered orally as a suspension, the pharmaceutical compositions can be prepared according to techniques well known in the art of pharmaceutical formulation and may contain a suspending agent, such as alginic acid or sodium alginate, bulking agent, such as microcrystalline cellulose, a viscosity enhancer, such as methylcellulose, and sweeteners/flavoring agents. Oral liquid preparations can contain conventional additives such as suspending agents, e.g., gelatin, glucose syrup, hydrogenated edible fats, methyl cellulose, sorbitol, and syrup; emulsifying agents, e.g., acacia, lecithin, or sorbitan monooleate; non-aqueous carriers (including edible oils), e.g., almond oil, fractionated coconut oil, oily esters such as glycerine, propylene glycol, or ethyl alcohol; preservatives such as methyl or propyl p-hydroxybenzoate or sorbic acid; and, if desired, conventional flavoring or coloring agents. When formulated as immediate release tablets, these compositions can contain dicalcium phosphate, lactose, magnesium stearate, microcrystalline cellulose, and starch and/or other binders, diluents, disintegrants, excipients, extenders, and lubricants.

If oral administration is desired, the laminin, laminin composition, or other therapeutic substance can be provided in a composition that protects it from the acidic environment of the stomach. For example, the laminin, laminin composition, or other therapeutic agent can be formulated with an enteric coating that maintains its integrity in the stomach and releases the active compound in the intestine. The laminin, laminin composition, or other therapeutic agent can also be formulated in combination with an antacid or other such ingredient.

Oral compositions generally include an inert diluent or an edible carrier and can be compressed into tablets or enclosed in gelatin capsules. For the purpose of oral therapeutic administration, the laminin, laminin composition, or other therapeutic substance can be incorporated with excipients and used in the form of capsules, tablets, or troches. Pharmaceutically compatible adjuvant materials or binding agents can be included as part of the composition.

The capsules, pills, tablets, troches, and the like can contain any of the following ingredients or compounds of a similar nature: a binder such as, but not limited to, acacia, corn starch, gelatin, gum tragacanth, polyvinylpyrrolidone, or sorbitol; a filler such as calcium phosphate, glycine, lactose, microcrystalline cellulose, or starch; a disintegrating agent such as, but not limited to, alginic acid and corn starch; a lubricant such as, but not limited to, magnesium stearate, polyethylene glycol, silica, or talc; a gildant, such as, but not limited to, colloidal silicon dioxide; a sweetening agent such as sucrose or saccharin; disintegrants such as potato starch; dispersing or wetting agents such as sodium lauryl sulfate; and a flavoring agent such as peppermint, methyl salicylate, or fruit flavoring.

When the dosage unit form is a capsule, it can contain, in addition to material of the above type, a liquid carrier, such as a fatty oil. In addition, dosage unit forms can contain various other materials that modify the physical form of the dosage unit, for example, coatings of sugar and other enteric agents. The laminin, laminin composition, or other therapeutic agent can also be administered as a component of an elixir, suspension, syrup, wafer, tea, chewing gum, or the like. A syrup may contain, in addition to the active compounds, sucrose or glycerin as a sweetening agent and certain preservatives, dyes and colorings, and flavors.

When administered orally, the compounds can be administered in usual dosage forms for oral administration. These dosage forms include the usual solid unit dosage forms of tablets and capsules as well as liquid dosage forms such as solutions, suspensions, and elixirs. When the solid dosage forms are used, they can be of the sustained release type so that the compounds need not be administered less frequently.

As explained elsewhere in the present disclosure, surprisingly and contrary to prior expectations, it has been determined that laminin is readily absorbed by subjects and made physiologically available. For example, it has been demonstrated that laminin injected into the stomach of a subject is incorporated systemically in the subject, such as in diverse muscle groups. Intraperitoneal injection also produced systemic distribution of laminin, including distribution of laminin to the diaphragm, gastrocnemius muscles, and cardiac muscles. In further examples, when administration occurs by intramuscular injection, the laminin has been found to permeate to nearby muscle groups. Accordingly, it is believed the administration of laminin may not suffer from some of the severe delivery problems which have plagued other proteins, particularly large proteins. Examples of methods and compositions for administering therapeutic substances which include proteins include those discussed in Banga, *Therapeutic Peptides and Proteins: Formulation, Processing, and Delivery Systems* 2ed. (2005); Mahato, *Biomaterials for Delivery and Targeting of Proteins and Nucleic Acids* (2004); McNally, *Protein Formulation and Delivery*, 2ed. (2007); and Kumar et al., "Novel Delivery Technologies for Protein and Peptide Therapeutics," *Current Pharm. Biotech.*, 7:261-276

(2006); each of which is incorporated by reference herein to the extent not inconsistent with the present disclosure.

"Inhibiting" a disease or condition refers to inhibiting the development of a disease or condition, for example, in a subject who is at risk for a disease or who has a particular disease. Particular methods of the present disclosure provide methods for inhibiting muscular dystrophy. "Treatment" refers to a therapeutic intervention that ameliorates a sign or symptom of a disease or condition after it has begun to develop. As used herein, the term "ameliorating," with reference to a disease or condition, refers to any observable beneficial effect of the treatment. The beneficial effect can be evidenced, for example, by a delayed onset of clinical symptoms of the disease or condition in a susceptible subject, a reduction in severity of some or all clinical symptoms of the disease or condition, a slower progression of the disease or condition, a reduction in the number of relapses of the disease or condition, an improvement in the overall health or well-being of the subject, by other parameters well known in the art that are specific to the particular disease or condition, and combinations of such factors.

"Therapeutically-effective amount" refers to an amount effective for lessening, ameliorating, eliminating, preventing, or inhibiting at least one symptom of a disease, disorder, or condition treated and may be empirically determined. In various embodiments of the present disclosure, a "therapeutically-effective amount" is a "muscle regeneration promoting-amount," an amount sufficient to achieve a statistically significant promotion of tissue or cell regeneration, such as muscle cell regeneration, compared to a control.

In particular, indicators of muscular health, such as muscle cell regeneration, maintenance, or repair, can be assessed through various means, including monitoring markers of muscle regeneration, such as transcription factors such as Pax7, Pax3, MyoD, MRF4, and myogenin. For example, increased expression of such markers can indicate that muscle regeneration is occurring or has recently occurred. Markers of muscle regeneration, such as expression of embryonic myosin heavy chain (eMyHC), can also be used to gauge the extent of muscle regeneration, maintenance, or repair. For example, the presence of eMyHC can indicate that muscle regeneration has recently occurred in a subject.

Muscle cell regeneration, maintenance, or repair can also be monitored by determining the girth, or mean cross sectional area, of muscle cells or density of muscle fibers. Additional indicators of muscle condition include muscle weight and muscle protein content. Mitotic index (such as by measuring BrdU incorporation) and myogenesis can also be used to evaluate the extent of muscle regeneration.

In particular examples, the improvement in muscle condition, such as regeneration, compared with a control is at least about 10%, such as at least about 30%, or at least about 50% or more.

In some implementations, the effective amount of laminin or laminin composition is administered as a single dose per time period, such as every three or four months, month, week, or day, or it can be divided into at least two unit dosages for administration over a period. Treatment may be continued as long as necessary to achieve the desired results. For instance, treatment may continue for about 3 or 4 weeks up to about 12-24 months or longer, including ongoing treatment. The compound can also be administered in several doses intermittently, such as every few days (for example, at least about every two, three, four, five, or ten days) or every few weeks (for example at least about every two, three, four, five, or ten weeks).

Particular dosage regimens can be tailored to a particular subject, condition to be treated, or desired result. For example, when the methods of the present disclosure are used to treat muscular dystrophy or similar conditions, an initial treatment regimen can be applied to arrest the condition. Such initial treatment regimen may include administering a higher dosage of the laminin or laminin composition, or administering such material more frequently, such as daily. After a desired therapeutic result has been obtained, such as a desired level of muscle regeneration, a second treatment regimen may be applied, such as administering a lower dosage or laminin or laminin composition or administering such material less frequently, such as monthly, bi-monthly, quarterly, or semi-annually. In such cases, the second regimen may serve as a "booster" to restore or maintain a desired level of muscle regeneration. Similar treatment regimens may be used for other subjects with reduced or impaired muscle regeneration capabilities, such as geriatric subjects.

When particular methods of the present disclosure are used to prevent or mitigate muscle damage, such as damage caused by exertion or injury, the subject is typically treated a sufficient period of time before the exertion or injury in order to provide therapeutic effect. For example, the subject may be treated at least about 24 hours before the expected activity or potential injury, such as at least about 48 hours, about 72 hours, about 1 week, about 2 weeks, about three weeks, or about 4 weeks or more prior.

When embodiments of the method of the present disclosure are used to promote wound healing, the laminin, laminin composition, or other therapeutic substance can be applied directly to, or proximately to, the area to be treated. For example, the substance can be injected into or near the area. In further examples, the substance can be applied topically to the area to be treated. Treatment is typically initiated prior to the injury to several weeks following the injury. In more specific implementations, the treatment is initiated between about 12 and about 72 hours following injury, such as between about 24 and about 48 hours following injury. In some cases, a single administration of the substance is effective to provide the desired therapeutic effect. In further examples, additional administrations are provided in order to achieve the desired therapeutic effect.

Amounts effective for various therapeutic treatments of the present disclosure may, of course, depend on the severity of the disease and the weight and general state of the subject, as well as the absorption, inactivation, and excretion rates of the therapeutically-active compound or component, the dosage schedule, and amount administered, as well as other factors known to those of ordinary skill in the art. It also should be apparent to one of ordinary skill in the art that the exact dosage and frequency of administration will depend on the particular laminin, laminin composition, or other therapeutic substance being administered, the particular condition being treated, the severity of the condition being treated, the age, weight, general physical condition of the particular subject, and other medication the subject may be taking. Typically, dosages used in vitro may provide useful guidance in the amounts useful for in vivo administration of the pharmaceutical composition, and animal models may be used to determine effective dosages for treatment of particular disorders. For example, mouse models of muscular dystrophy may be used to determine effective dosages that can then be translated to dosage amount for other subjects, such as humans, as known in the art. Various considerations in dosage determination are described, e.g., in Gilman et al., eds., *Goodman And Gilman's: The Pharmacological Bases of Therapeutics*, 8th ed., Pergamon Press (1990); and *Remington's Pharma-*

*ceutical Sciences,* 17th ed., Mack Publishing Co., Easton, Pa. (1990), each of which is herein incorporated by reference to the extent not inconsistent with the present disclosure.

In specific examples, the laminin or laminin composition is administered to a subject in an amount sufficient to provide a dose of laminin of between about 10 fmol/g and about 500 nmol/g, such as between about 2 nmol/g and about 20 nmol/g or between about 2 nmol/g and about 10 nmol/g. In additional examples, the laminin or laminin composition is administered to a subject in an amount sufficient to provide a dose of laminin of between about 0.01 µg/kg and about 1000 mg/kg or between about 0.1 mg/kg and about 1000 mg/kg, in particular examples this amount is provided per day or per week. In another example, the laminin or laminin composition is administered to a subject in an amount sufficient to provide a dose of laminin of between about 0.2 mg/kg and about 2 mg/kg. In further examples, the laminin or laminin composition is administered to a subject in an amount sufficient to provide a concentration of laminin in the administrated material of between about 5 nM and about 500 nM, such as between about 50 nM and about 200 nm, or about 100 nM.

The above term descriptions are provided solely to aid the reader, and should not be construed to have a scope less than that understood by a person of ordinary skill in the art or as limiting the scope of the appended claims.

Description

Generally, the present disclosure provides embodiments of a method and composition for enhancing cell or tissue repair, regeneration, or maintenance, including prospective treatment against subsequent injury, damage, or disease. In various embodiments, the present disclosure provides methods of treating muscular dystrophy, enhancing muscle repair following injury or damage, or reducing the severity of muscle injury or damage. Further embodiments provide a method for enhancing wound healing.

In some embodiments, the method includes administering an effective amount of laminin or a composition which includes an effective amount of laminin. In a specific implementation of the method, the laminin is laminin-1. In a further specific implementation of the method, the laminin is laminin-2 or laminin-4.

Without intending to be limited to a particular mechanism of action, laminin is believed to aid muscle regeneration by activating satellite cells to proliferate and differentiate into new muscle cells and myotubes. Accordingly, muscle repair may be enhanced compared with the subject's native condition.

Particularly when the methods are used to treat muscular dystrophy, and again without being bound by a theory of operation, laminin may also aid in binding components of the extracellular matrix, such as binding to dystrophin or α7β1 integrin. For example, in Duchenne muscular dystrophy, increased amounts of laminin may aid in forming connections with the basement membrane through binding of α7β1 integrin or another receptor, such as utrophin, which is homologous to dystrophin. Administration of laminin may also upregulate expression of one or more components of the costameric network, such as utrophin or α7β1 integrin, potentially providing additional linkage points between the extracellular matrix and the remainder of the costamere. Laminin may also provide a structural environment to improve tissue integrity.

In further embodiments, the present disclosure provides methods for promoting muscle regeneration. Muscle regeneration may benefit, for example, geriatric or other patient populations with reduced muscle repair capability, or simply speed the muscle repair process for otherwise physiologically unimpaired patients. In particular implementations, administration of laminin can aid muscle repair, or reduction of muscle damage, in athletes or others having activity-induced muscle injury or damage. In yet further implementations, muscle repair in patients suffering from muscle damage, such as through accident or injury, can be augmented by administration of laminin.

In various examples of the embodiments of the present disclosure, the laminin or laminin composition is administered with one or more other components, such as components of the extracellular matrix. For example, the additional substance can include aggrecan, angiostatin, cadherins, collagens (including collagen I, collagen III, or collagen IV), decorin, elastin, enactin, endostatin, fibrin, fibronectin, osteopontin, tenascin, thrombospondin, vitronectin, and combinations thereof. Biglycans, glycosaminoglycans (such as heparin), glycoproteins (such as dystroglycan), proteoglycans (such as heparan sulfate), and combinations thereof can also be administered. A particular laminin can be administered with other forms of laminin, laminin analogs, laminin derivatives, or a fragment of any of the foregoing.

Growth stimulants may be added in conjunction with the laminin or laminin composition. Examples of growth stimulants include cytokines, polypeptides, and growth factors such as brain-derived neurotrophic factor (BDNF), CNF (ciliary neurotrophic factor), EGF (epidermal growth factor), FGF (fibroblast growth factor), glial growth factor (GGF), glial maturation factor (GMF) glial-derived neurotrophic factor (GDNF), hepatocyte growth factor (HGF), insulin, insulin-like growth factors, kerotinocyte growth factor (KGF), nerve growth factor (NGF), neurotropin-3 and -4, PDGF (platelet-derived growth factor), vascular endothelial growth factor (VEGF), and combinations thereof.

Additional therapeutic agents can be added to enhance the therapeutic effect of the laminin or laminin composition. For example, a source of muscle cells can be added to aid in muscle regeneration and repair. In some aspects of the present disclosure, satellite cells are administered to a subject in combination with laminin therapy. U.S. Patent Publication 2006/0014287, incorporated by reference herein to the extent not inconsistent with the present disclosure, provides methods of enriching a collection of cells in myogenic cells and administering those cells to a subject.

In further aspects, stem cells, such as adipose-derived stem cells, are administered to the subject. Suitable methods of preparing and administering adipose-derived stem cells are disclosed in U.S. Patent Publication 2007/0025972, incorporated by reference herein to the extent not inconsistent with the present disclosure. Additional cellular materials, such as fibroblasts, can also be administered, in some examples.

The following examples are provided to illustrate certain particular features and/or embodiments. These examples should not be construed to limit the invention to the particular features or embodiments described.

EXAMPLE 1

Materials and Methods

Animals

Wild-type (C57BL/6), α7 integrin-null (C57BL/6 background), and Nestin-GFP mouse (C57BL/6 background) used in these studies were euthanized in accordance with protocols approved by the University of Nevada, Reno and University of Washington, Seattle Institutional Animal Care and Use Committees.

Histology

Tibialis anterior (TA) muscles were embedded in Optimal Cutting Temperature (OCT) (Tissue-Tek; Sakura Finetek, Torrance, Calif., United States) and 10 µm cryosections were cut (≧50 µm apart) using a Leica CM1850 cryostat placed on Surgipath microscope slides (Surgipath Medical Industries, Richmond, Ill.). Tissue sections were stained using hematoxylin and eosin (H&E) as previously described in Rooney et al., "Severe muscular dystrophy in mice that lack dystrophin and alpha7 integrin," *J. Cell Sci.* 119:2185-2195 (2006), incorporated by reference herein to the extent not inconsistent with the present disclosure. Central myonuclei in regenerating muscles were counted at 630× magnification by brightfield microscopy. The number of central nuclei per muscle fiber was determined by counting a minimum of 1000 muscle fibers per animal. At least five animals from each genotype were analyzed. In addition, the cross-sectional area was examined in a minimum of 5000 muscle fibers per group per time point. Results were reported as the average fiber cross-sectional area.

Immunofluorescence

TA muscles were embedded in Tissue-TEK Optimal Cutting Temperature compound (Sakura Finetek USA Inc., Torrance, Calif.). Sections were cut at 10 µm using a Leica CM1850 cryostat and placed onto Surgipath microscope slides (Surgipath Medical Industries, Richmond, Ill.). Laminin-$\alpha$2 chain was detected with a 1:500 dilution of rabbit anti-laminin-$\alpha$2 (2G) polyclonal antibody (a kind gift from Peter Yurchenco, Robert Wood Johnson Medical School, Department of Pathology, Piscataway, N.J.). The laminin-$\alpha$1 chain was detected using an anti-laminin-$\alpha$1 antibody (sc-5582, Santa Cruz Biotechnology, Santa Cruz, Calif.). Primary rabbit antibodies were detected with a 1:500 dilution of fluorescein isothiocyanate (FITC)-conjugated anti-rabbit secondary antibody.

For mouse monoclonal antibodies, endogenous mouse immunoglobulin was blocked with a mouse-on-mouse (MOM) kit (Vector Laboratories, Burlingame, Calif.). Expression of MyoD and Pax7 was detected using 5 µg/ml anti-MyoD and anti-Pax7 (Developmental Studies Hybridoma Bank (DSHB), Iowa City, Iowa). eMyHC was detected as previously described (Rooney et al., 2006). A 1 µg/ml concentration of tetramethylrhodamine-conjugated wheat-germ agglutinin (WGA) (Molecular Probes, Eugene, Oreg.) was used to define muscle fibers. Fluorescence was observed with a Zeiss Axioskop 2 Plus fluorescent microscope and images were captured with a Zeiss AxioCam HRc digital camera and Axiovision 4.1 software (all available from Carl Zeiss MicroImaging, Thornwood, N.Y.). Multiple adjacent sections were analyzed within 20 random, non-overlapping microscopic fields per animal at 630× magnification.

Single myofibers were isolated from the Extensor Digitorum Longus muscle of 10 week old nestin-GFP transgenic mice after collagenase digestion and cultured individually in Matrigel-coated wells as previously described (Shefer, et al., "Skeletal muscle satellite cells can spontaneously enter an alternative mesenchymal pathway," *J. Cell Sci.* 117:5393-5404 (2004); Shefer, et al., "Isolation and culture of skeletal muscle myofibers as a means to analyze satellite cells," *Methods Mol. Biol.* 290:281-304 (2005); each of which is incorporated by reference herein to the extent not inconsistent with the present disclosure). Adherent single myofibers were fixed in 4% paraformaldehyde and incubated with 1:1000 dilution of anti-$\alpha$7 integrin rat monoclonal antibody (CA5.5) (Sierra BioSource, Morgan Hill, Calif.). The anti-$\alpha$7 integrin rat antibody was detected using rhodamine labeled anti-rat secondary antibody. Both GFP and rhodamine fluorescence were detected using an inverted fluorescent microscope (Nikon eclipse, TE2000-S, Nikon Instruments, Inc., Melville, N.Y.) and images were acquired with a CoolSNAP$_{ES}$ monochrome CCD camera (Princeton Instruments Inc., Trenton, N.J.) controlled by MetaVue Imaging System (Universal Imaging Corporation, Downingtown, Pa.).

Evan's Blue Dye Assay

Mice were injected intraperitoneally with 50 µl of a 10 mg/ml solution of sterile Evans blue dye (EBD) solution per 10 g of body weight. After 3 hours, the TA muscle was harvested and flash-frozen in liquid nitrogen. 10 µm cryosections were placed on microscope slides and fixed in 4% paraformaldehyde. Muscle fibers were outlined by incubating tissue sections with Oregon Green-488-conjugated wheat germ agglutinin (2 µg/ml, Molecular Probes, Eugene, Oreg.). A minimum of 1000 fibers per animal were counted to determine the percentage of muscle fibers positive for EBD. At least four animals from each genotype were analyzed. Images were captured and counting conducted at 630× magnification.

Bromodeoxyuridine (BrdU) Incorporation

BrdU (500 mg/kg) was injected intraperitoneally at 72 hours, 48 hours and 24 hours prior to muscle harvesting. Muscle cryosections were fixed in 95% ethanol for 1 minute. Sections were then rinsed in phosphate-buffered saline (PBS) and treated with 2N hydrochloric acid (HCl) for 20 minutes. The sections were neutralized in 50 mM sodium chloride (NaCl) for 20 minutes, followed by incubation in 100 mM Tris-HCl for 20 minutes and rinsed in PBS. Tissue was incubated in anti-BrdU antibody (G3G4, 1:1000, Developmental Studies Hybridoma Bank (DSHB), Iowa City, Iowa) for 1 hour, washed in PBS and mounted in Vectashield (Vector Labs, Burlingame, Calif.).

Cardiotoxin-Induced Muscle Injury

Mice were anesthetized with avertin (0.25 µl/g of body weight) and 100 µl of a 10 µm cardiotoxin solution (C3987, Sigma, St. Louis, Mo.) in PBS was injected into the left TA muscle of 5-week-old male wild-type and $\alpha 7^{-/-}$ mice. The right TA muscles were injected with 100 µl of PBS and used as a control. The mice were euthanized and muscles harvested at 4, 7, 10, and 28 days after cardiotoxin injection for analysis.

Laminin-111 Injections

Natural mouse laminin (Invitrogen, Carlsbad, Calif.) at 100 nM in PBS was injected into the left TA muscle of anesthetized wild-type and $\alpha 7^{-/-}$ mice three days prior to cardiotoxin injection. The right TA muscles were injected with 100 µl of PBS and served as controls. The muscles were harvested at 0, 4, 7, 10 and 28 days post-cardiotoxin injection for analysis.

Statistical Analysis

All averaged data are reported as the mean±standard deviation. Comparisons between multiple groups were performed by one-way-analysis of variance (ANOVA) for parametric data or by Kruskal-Wallis one-way-analysis of variance on ranks for non-parametric data using SigmaStat 1.0 software (Jandel Corporation, San Rafael, Calif.). P<0.05 was considered statistically significant.

Integrin Expression in Quiescent Satellite Cells

To confirm that the $\alpha$7 integrin is expressed in satellite cells, isolated myofibers from nestin-GFP transgenic mice were subjected to immunofluorescence using an anti-$\alpha$7 integrin monoclonal antibody (FIG. 1). Nestin-GFP is specifically expressed in quiescent satellite cells. All nestin-GFP positive cells on the myofiber surface were also positive for the $\alpha$7 integrin (FIG. 1). Image analysis indicated stronger localization of the $\alpha$7 integrin on the basal surface of the satellite cells. These data confirm that quiescent satellite cells express the α7 integrin and localization is enriched on the basal surface facing the muscle myofiber.

Muscle Repair in Integrin Null Mice

Figure 2:
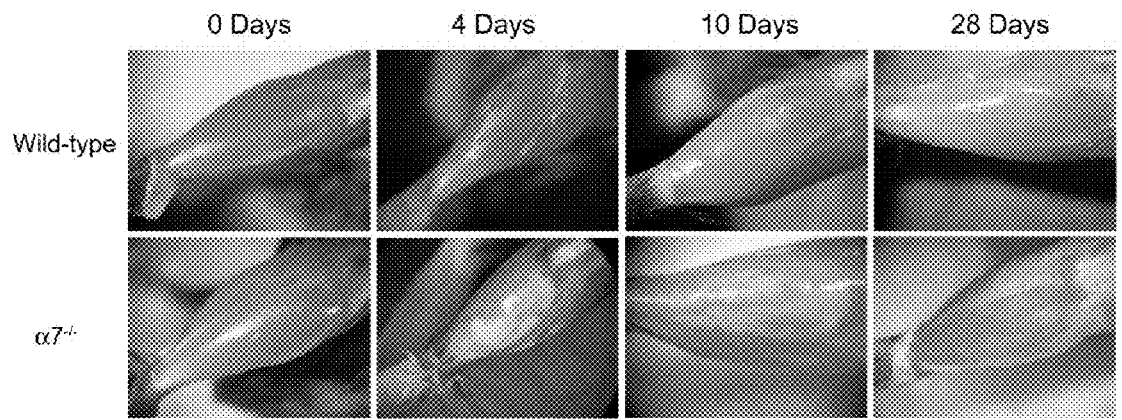
FIG. 2 is photographs of the tibialis anterior muscle of wild-type and α7 integrin null mice 4, 10, and 28 days after cardiotoxin-induced injury.

Recent studies suggest the α7 integrin plays a role in satellite cell activation and/or proliferation. To examine if the α7β1 integrin is required for muscle repair, the tibialis anterior (TA) muscle of wild-type and α7 integrin null mice were subjected to cardiotoxin-induced injury and examined 4, 10 and 28 days later (FIG. 2). Four days after cardiotoxin injury, wild-type TA muscle appeared healthy and this appearance persisted for 28 days. In contrast, α7 integrin null muscle exhibited large white regions of damaged muscle at 4 and 10 days post-injury. At 28 days, regions of muscle damage were still clearly evident in α7 integrin null muscle. These data suggest loss of the α7 integrin in skeletal muscle results in a profound delay in muscle regeneration.

Loss of the α7 Integrin Results in Decreased Membrane Integrity after Injury

Figure 3:
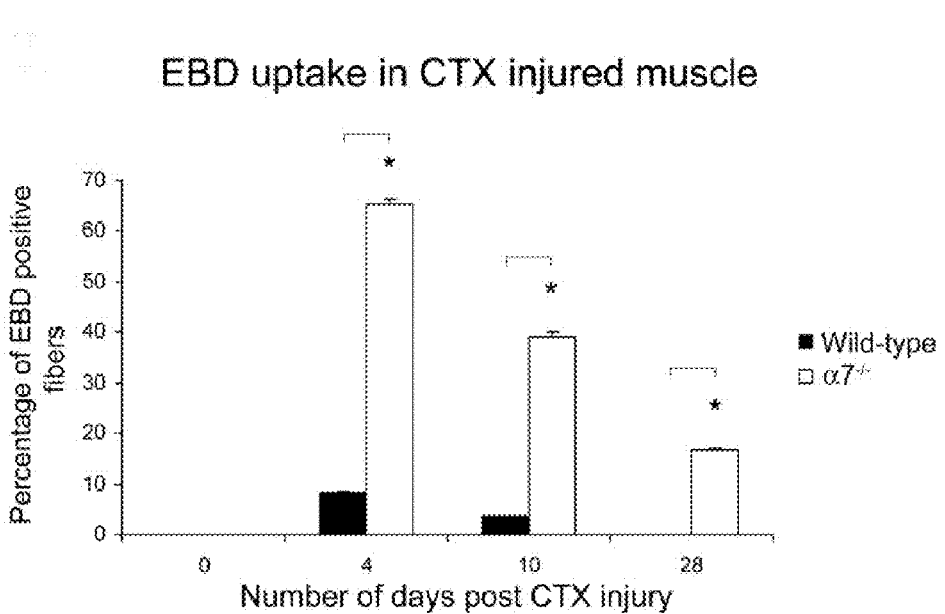
FIG. 3 provides a graph illustrating Evan's blue dye uptake by wild-type and α7 integrin null mice.

To examine membrane integrity after cardiotoxin treatment, wild-type and α7 integrin null mice were injected with Evan's blue dye (EBD). EBD uptake was absent in both groups prior to cardiotoxin injection (FIG. 3). Although α7 integrin null muscle was negative for EBD uptake prior to cardiotoxin injection, 7-fold more myofibers were EBD positive at day 4 compared to wild-type. At day 4 post-injury, 8.5% of wild-type and 66% of α7 integrin null myofibers were EBD positive. After 10 days, less than 4% of wild-type myofibers were positive for EBD uptake, while 40% of α7 integrin deficient myofibers were EBD positive. At 28 days post-cardiotoxin injection, 17% of α7 integrin null muscle fibers were still EBD positive, while EBD was not observed in wild-type muscle ($P<0.05$), (FIG. 3). These results indicate loss of the α7 integrin results in increased sarcolemmal fragility after cardiotoxin-induced injury.

Reduced Muscle Repair in α7 Integrin Null Mice

Figure 4:
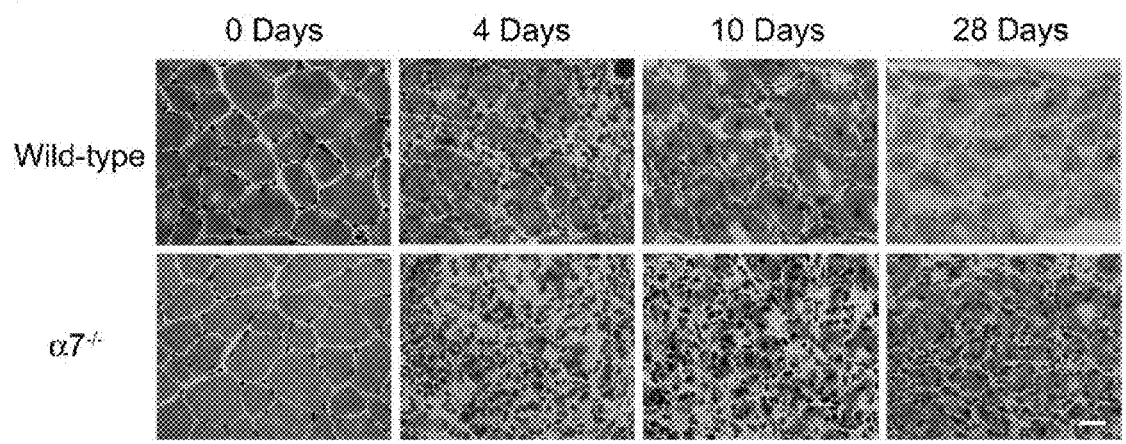
FIG. 4 is photomicrographs of hematoxylin and eosin stainings of tissue sections from wild-type and α7 integrin null mice.

Hematoxylin and Eosin (H&E) staining was used to examine mononuclear cell infiltrate and centrally located nuclei after cardiotoxin-induced injury (FIG. 4, scale bar indicates 10 μm). Four days after cardiotoxin-injury, wild-type muscle exhibited mononuclear cell infiltrate and myofibers containing centrally located nuclei (FIG. 4). By day 10, wild-type muscle exhibited little mononuclear infiltrate and most myofibers contained centrally located nuclei. By 28 days in wild-type muscle, repair was complete and most myofibers contained centrally located nuclei and little mononuclear cell infiltrate was evident. In contrast, after 4 days post-cardiotoxin-induced damage, α7 integrin null muscle exhibited extensive mononuclear cell infiltrate and hypotrophic muscle fibers which extended to 10 days post-cardiotoxin injury (FIG. 4). By 28 days, α7 integrin null muscle exhibited hypotrophic myofibers which contained centrally located nuclei and mononuclear cell infiltrate.

Figure 5:
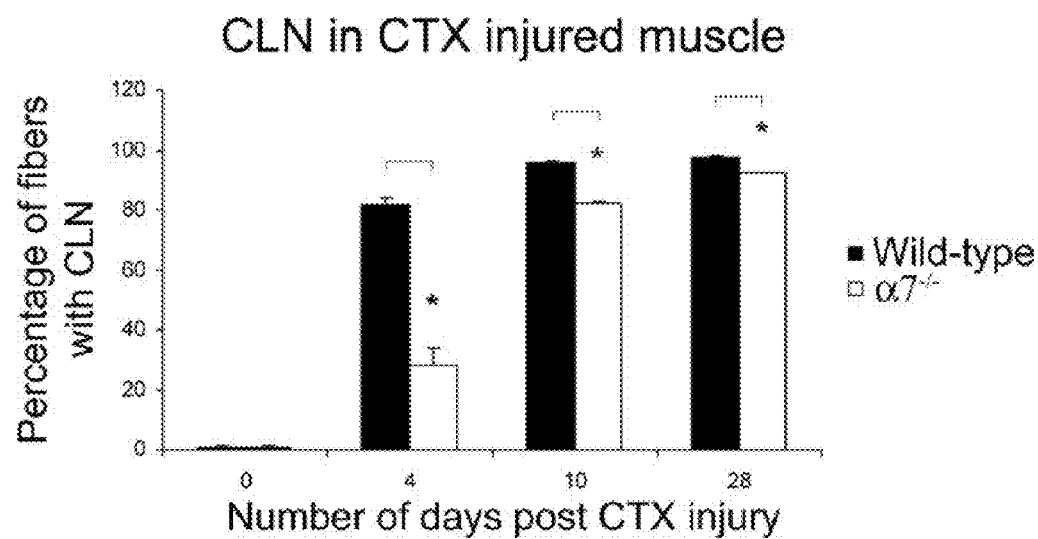
FIG. 5 provides a graph illustrating the percentage of centrally located nuclei in wild-type and α7 integrin null mice.

To quantify muscle repair, the percentage of myofibers with centrally located nuclei was calculated (FIG. 5). In wild-type mice, 81.8% of muscle fibers contained centrally located nuclei 4 days post-cardiotoxin injury. In contrast only 28.1% of muscle fibers in α7 integrin null muscle were positive for centrally located nuclei ($P<0.05$). By 10 and 28 days, 95.5% and 97.5% of muscle fibers, respectively, in wild-type mice exhibited centrally located nuclei. By days 10 and 28, 82% and 95.5% of muscle fibers in α7 integrin null muscle, respectively, exhibited centrally located nuclei which were lower than wild-type ($P<0.05$). These results indicate loss of the α7 integrin results in delayed muscle regeneration.

Figure 6:
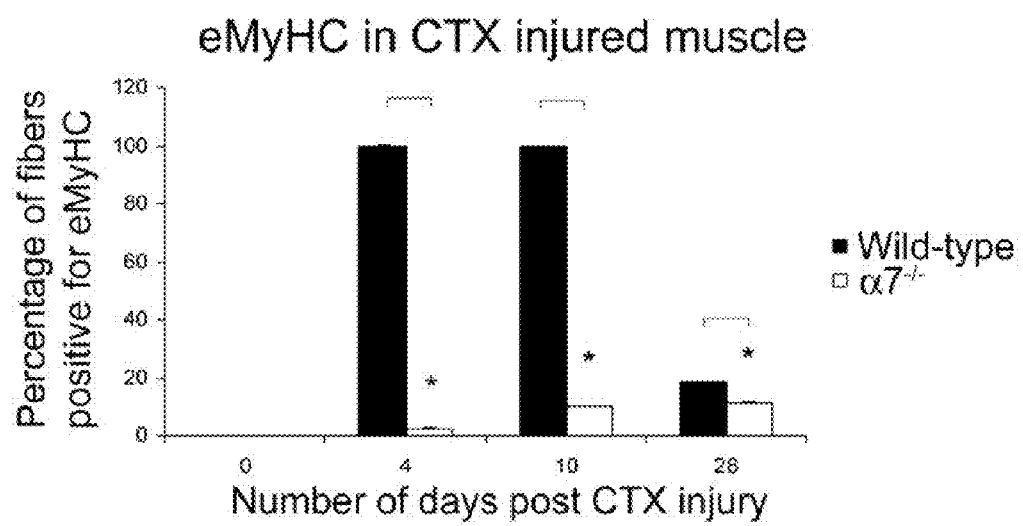
FIG. 6 provides a graph of embryonic myosin heavy chain expression in wild-type and α7 integrin null mice.

Embryonic myosin heavy chain (eMyHC) is transiently expressed after muscle repair and used as a marker for recent muscle regeneration. At day 0 there was an absence of eMyHC in both wild-type and α7 integrin null mice (FIG. 6). At 4 and 10 days post-cardiotoxin treatment, expression of eMyHC was detected in over 99% of wild-type muscle fibers (FIG. 6). In sharp contrast, only 2.2% and 9.9% of α7 integrin null muscle fibers expressed eMyHC at 4 and 10 days respectively after cardiotoxin-injury (FIG. 6). By day 28, only 11.3% of α7 integrin null myofibers were eMyHC positive, while 18.5% of wild-type muscle was eMyHC positive (*$P<0.001$). These results confirm that loss of the α7 integrin results in defective muscle repair as measured by the transient expression of eMyHC.

Figure 7:
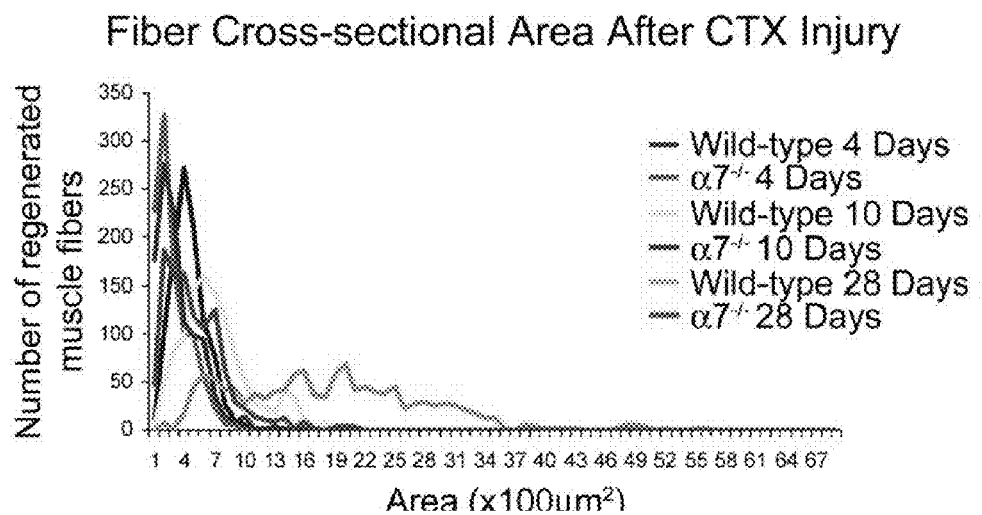
FIG. 7 provides a graph of myofiber cross-sectional area for wild-type and α7 integrin null mice.

Cardiotoxin Injury Results in Hypotrophic Muscle Fibers in α7 Integrin Null Mice To determine if loss of the α7 integrin affected muscle repair after injury, myofiber cross-sectional area was measured (FIG. 7). Regenerating muscle fibers in wild-type mice were 31% larger than α7 integrin null muscle fibers 4 days post-cardiotoxin injury (FIG. 7). At day 10, regenerating wild-type myofibers were 45.1% larger compared to α7 integrin-deficient muscle fibers (FIG. 7). By day 28, wild-type muscle displayed muscle fiber size variation. However this was in contrast to the α7 integrin null muscle which continued to display small cross-sectional areas, with the vast majority of fibers in the 100-600 $\mu m^2$ range. These results indicate loss of the α7 integrin results in reduced regenerative capacity, giving rise to hypotrophic muscle fibers.

Figure 8:
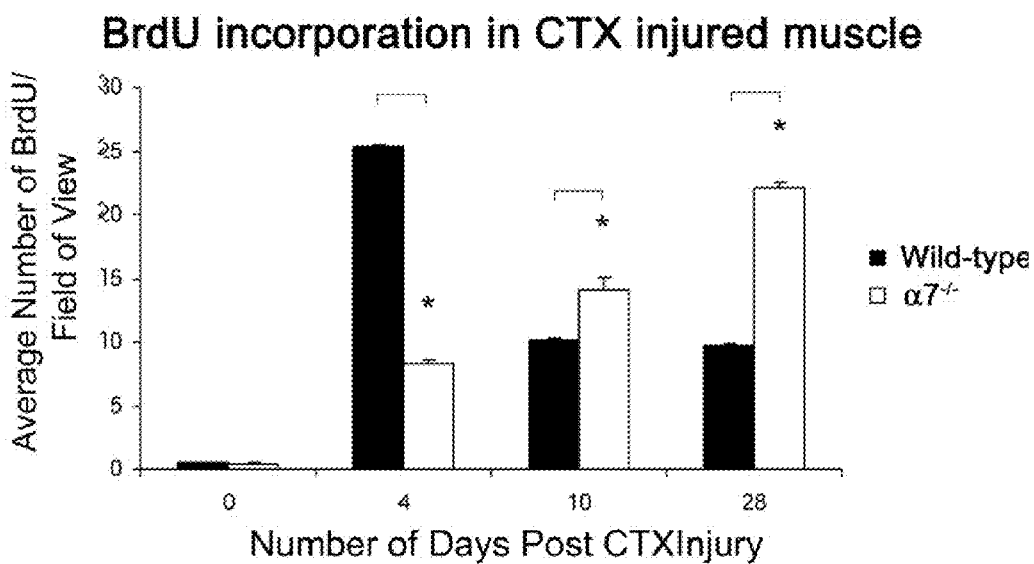
FIG. 8 provides a graph illustrating BrdU incorporation into wild-type and α7 integrin null mice.

Satellite Cell Proliferation and Differentiation are Reduced in α7 Integrin-Deficient Muscle after Injury To determine if satellite cell proliferation was decreased in α7 integrin null mice, incorporation of BrdU into the nuclei of satellite cells was quantified (FIG. 8). At 4 days post-injury, α7 integrin null muscle contained 3-fold fewer BrdU-positive nuclei compared to wild-type animals (FIG. 8). However, BrdU positive nuclei were increased in α7 integrin null mice at days 10 and 28 compare to wild-type (FIG. 8). These results show satellite cell proliferation is delayed in α7 integrin null muscle after cardiotoxin-induced injury.

Figure 9:
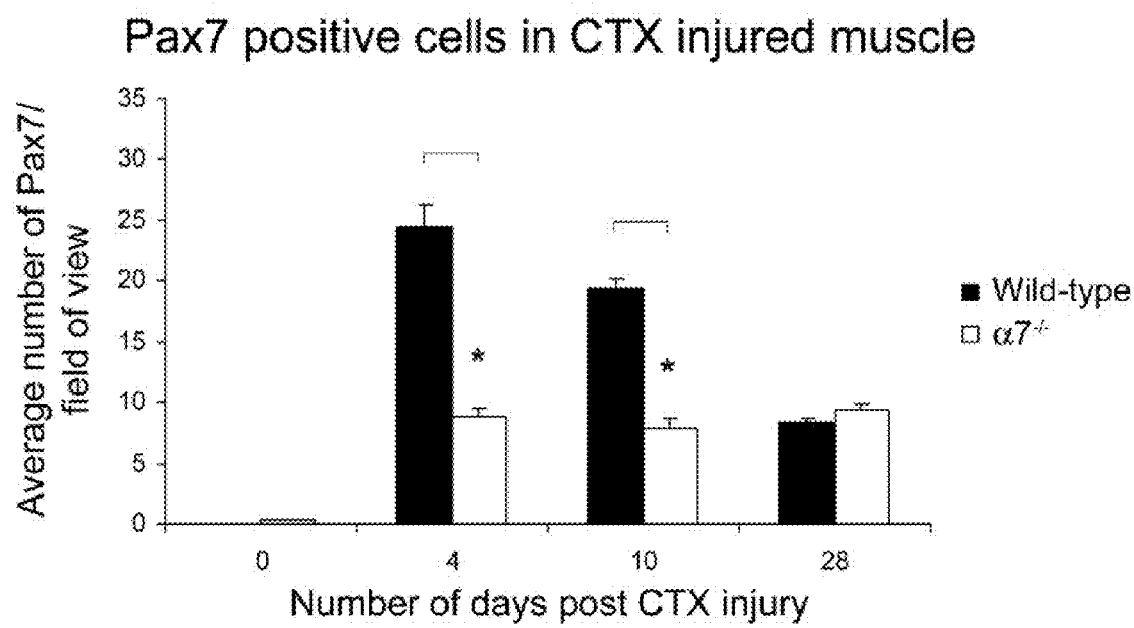
FIG. 9 provides a graph illustrating Pax7 expression in wild-type and α7 integrin null mice.

To examine if the developmental program regulating muscle repair was affected by the loss of the α7β1 integrin, expression of Pax7 and MyoD (FIGS. 9 & 10) was examined. Pax7 is expressed in both quiescent and activated satellite cells, while MyoD is expressed only in differentiated myoblasts. Compared to wild-type muscle, α7 integrin null mice exhibited 2- to 3-fold fewer Pax7 positive cells compared to wild-type at 4 and 10 days post-cardiotoxin injury (FIG. 9). By day 28, similar numbers of Pax7 positive cells were observed in wild-type and α7 integrin null mice.

Figure 10:
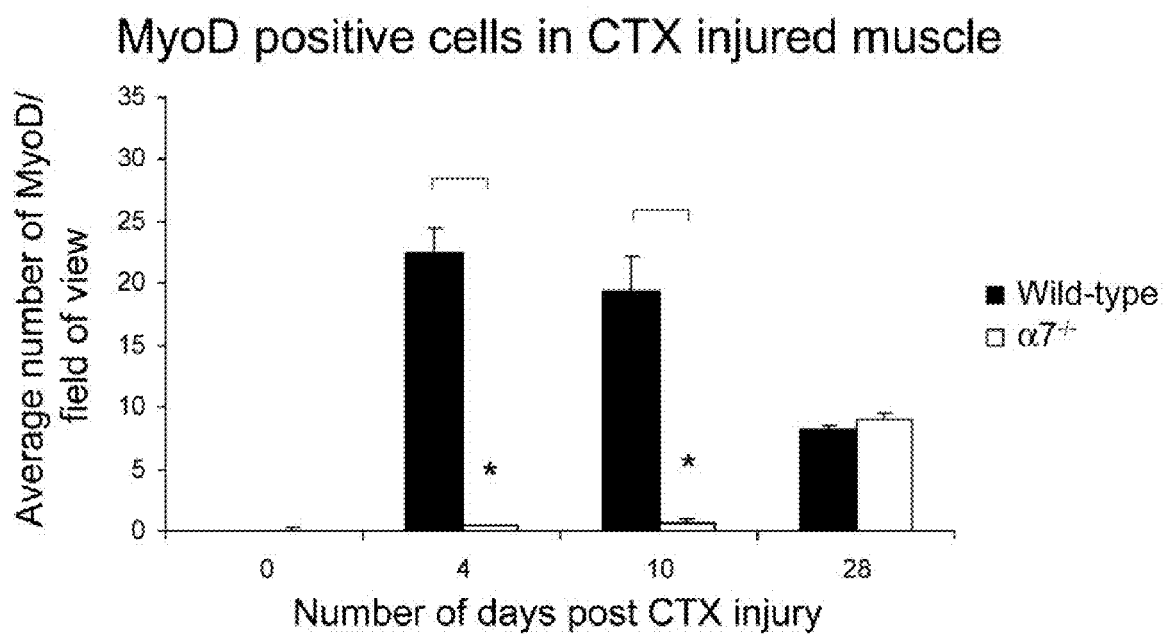
FIG. 10 provides a graph illustrating MyoD expression in wild-type and α7 integrin null mice.

Analysis of MyoD expression showed α7 integrin null muscle contained 28 and 50-fold fewer MyoD positive myoblasts compared to wild-type muscle at 4 and 10 days post-cardiotoxin induced damage, respectively (FIG. 10). By day 28 similar numbers of MyoD positive cells were observed in wild-type and α7 integrin null mice.

Together these results indicate loss of the α7 integrin results in fewer activated satellite cells in injured skeletal muscle and a delayed response in the developmental program that regulates myogenic differentiation.

Laminin Treatment of α7 Integrin Null Mice

Laminin-111 Treatment Restores Sarcolemmal Integrity in α7 Integrin Null Mice

Recent studies have shown loss of the α7 integrin results in reduced laminin expression. To explore if reduced laminin deposition could account for the defective muscle regenerative phenotype observed in α7 integrin null mice, the TA muscle was injected with laminin-111 three days prior to cardiotoxin injury.

Laminin-111 was injected into the TA muscle of 2 week old wild-type and α7 integrin null pups and tissue analyzed by immunofluorescence using an anti-laminin-α1 antibody. Muscle injected with PBS alone contained no laminin-111. By day 4, laminin-111 was abundantly in the extracellular matrix surrounding muscle fibers and persisted for more than 28 days. Titration of laminin-111 in cultured myofibers revealed increased toxicity at concentrations 200 nM and higher (data not shown).

Figure 11:
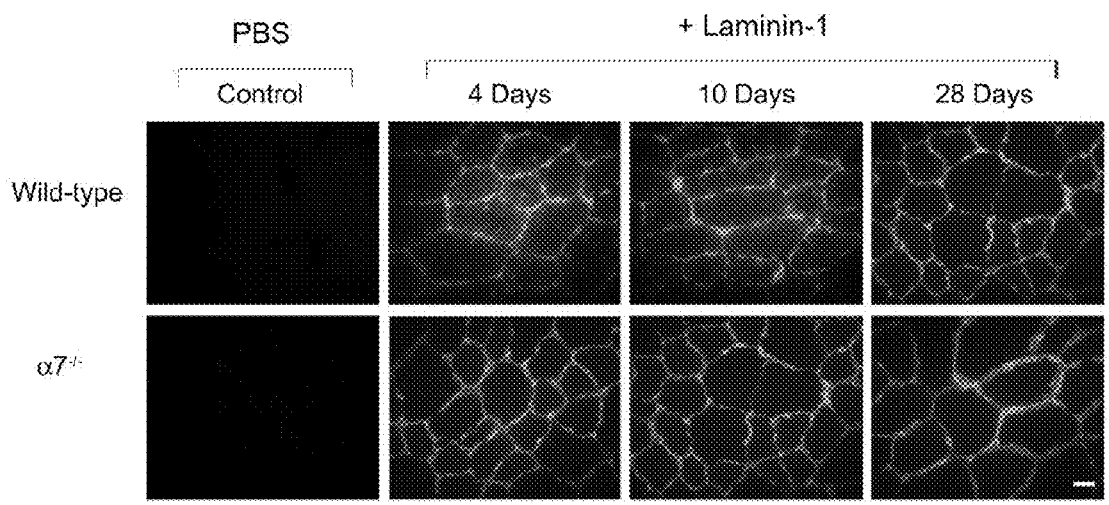
FIG. 11 is immunofluorescence images of myofibers isolated from wild-type and α7 integrin null mice treated with laminin-1.
Figure 12:
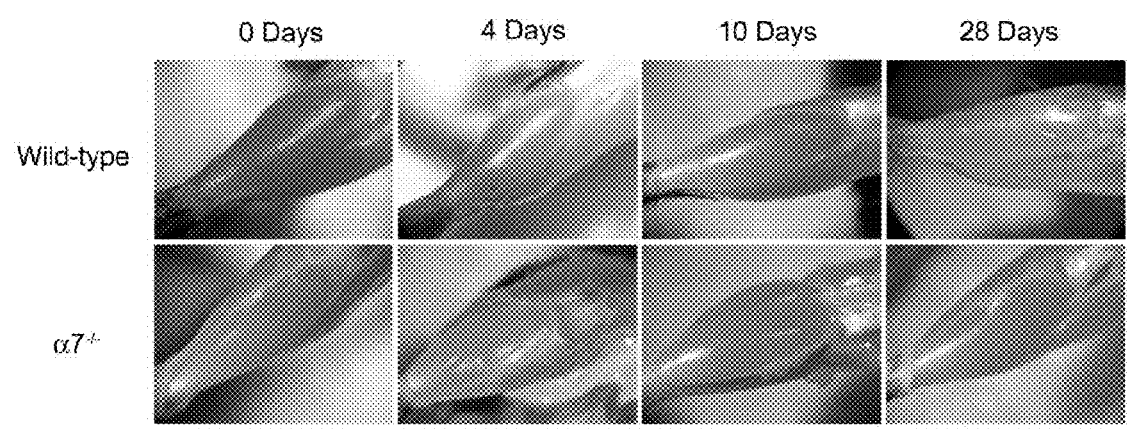
FIG. 12 is photographs of the tibialis anterior muscle of wild-type and α7 integrin null mice treated with laminin-1 4, 10, and 28 days after cardiotoxin-induced injury.

Surprisingly, the injected laminin-111 rapidly permeated the entire TA muscle within 24-72 hours (FIG. 11 and supplemental data) and was maintained throughout the muscle for at least 31 days (FIG. 11). At all time points after cardiotoxin-injury, α7 integrin null muscle treated with laminin-111 externally appeared identical to wild-type muscle (FIG. 12).

Figure 13:
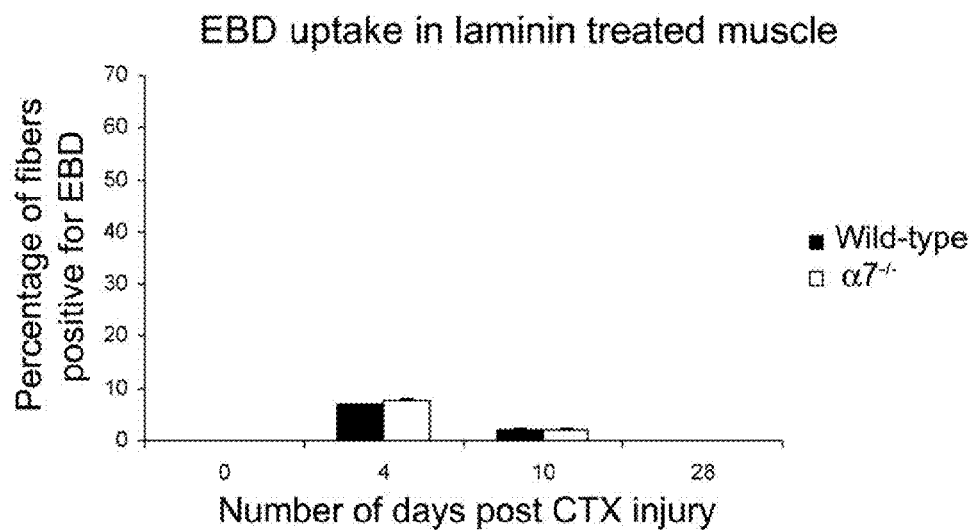
FIG. 13 provides a graph illustrating Evan's blue dye update by wild-type and α7 integrin null mice treated with laminin-1.

Analysis of EBD uptake after cardiotoxin-induced injury revealed no difference in the percentage of EBD-positive myofibers between laminin-treated wild-type or α7 integrin null muscle at all time points (FIG. 13). These results demonstrate that injection of laminin-111 prior to cardiotoxin-induced injury restored sarcolemmal integrity to α7 integrin null muscle.

Laminin Mediated Muscle Regeneration in Integrin Null Mice

Figure 14:
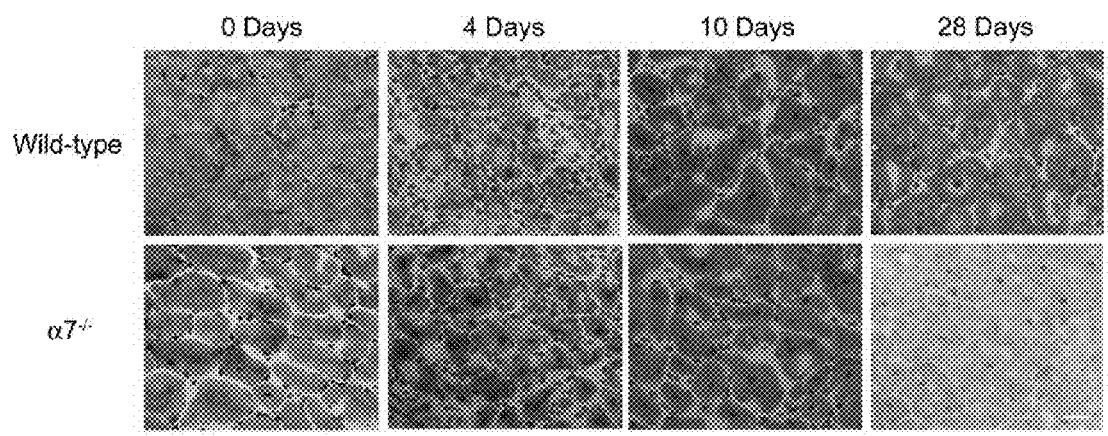
FIG. 14 is photomicrographs of hematoxylin and eosin stainings of tissue sections from wild-type and α7 integrin null mice treated with laminin-1.

To examine the ability of laminin-111 to improve muscle regeneration, 5-week-old wild-type and α7 integrin null TA muscle were injected with laminin and subjected to cardiotoxin-induced injury. Muscle sections were stained with H&E and mononuclear cell infiltrate and centrally located nuclei examined (FIG. 14). No difference in the myofiber size, centrally located nuclei or mononuclear cell infiltrate was observed in wild-type and α7 integrin null muscle treated with laminin-111 at 4, 10 or 28 days following injury (FIG. 14).

Figure 15:
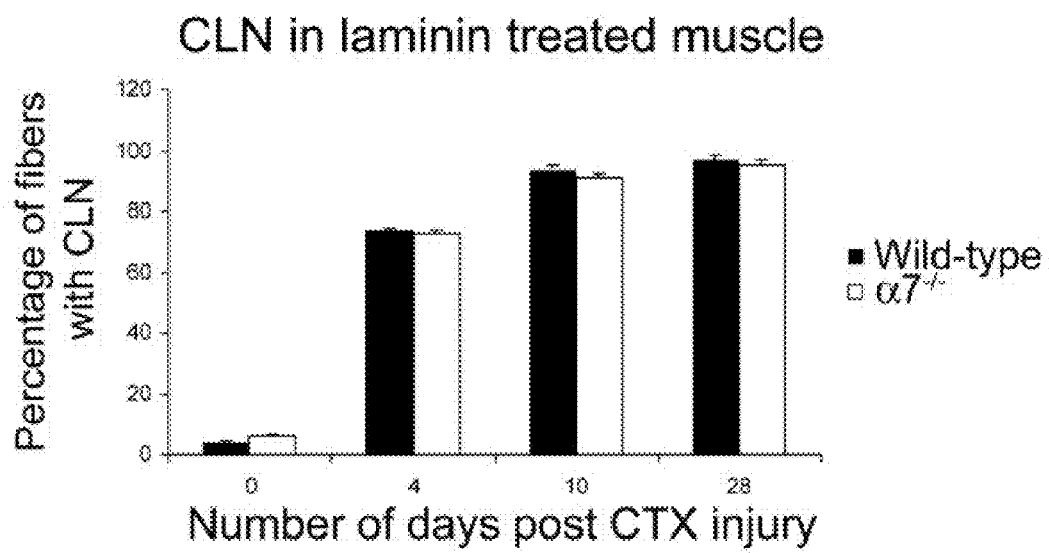
FIG. 15 provides a graph illustrating the percentage of centrally located nuclei in wild-type and α7 integrin null mice treated with laminin-1.

Quantitation of centrally located nuclei confirmed that laminin-111 treatment restored muscle regeneration to wild-type levels (FIG. 15). At all time points, analyzed percentages of centrally located nuclei in laminin-treated wild-type and α7 integrin null mice were not significantly different from each other. These results indicate that laminin-111 restored muscle repair in α7 integrin null muscle to wild-type levels.

Figure 16:
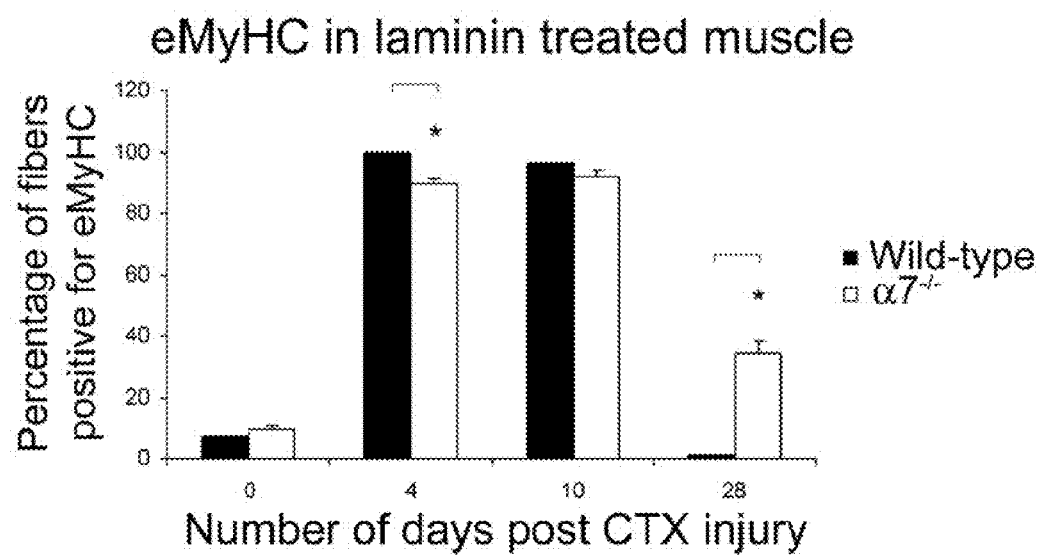
FIG. 16 provides a graph of embryonic myosin heavy chain expression in wild-type and α7 integrin null mice treated with laminin-1.

The ability of laminin-111 to restore regenerative capacity to α7 integrin null muscle was examined by assaying eMyHC expression (FIG. 16). At day 0, 7.3% of wild-type fibers and 9.7% of α7 integrin null fibers were eMyHC positive as a result of injection with laminin (FIG. 16). At 4 and 10 days after cardiotoxin treatment, wild-type and α7 integrin null muscle exhibited similar levels of eMyHC expression (FIG. 16). At 28 days post-injury, eMyHC was only present in negligible amounts in the wild-type muscle while 34.4% of myofibers in α7 integrin null muscle were positive for eMyHC (FIG. 16). These results demonstrate injection of laminin-111 greatly improved the regenerative capacity of α7 integrin null muscle.

Laminin Therapy Restores Myofiber Area in α7 Integrin Null Mice

Figure 17:
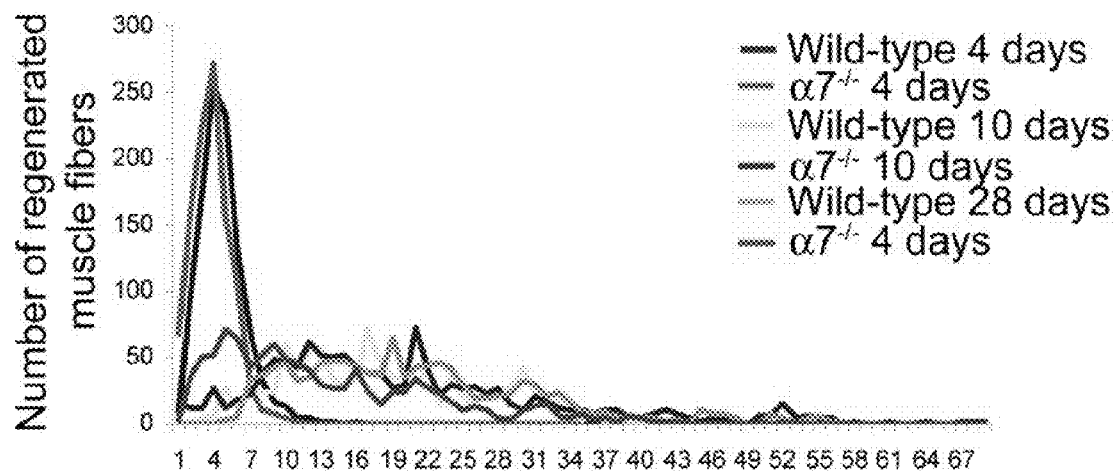
FIG. 17 provides a graph of myofiber cross-sectional area for wild-type and α7 integrin null mice treated with laminin-1.

Myofiber cross-sectional area was examined in laminin-treated wild-type and α7 integrin null mice before and after cardiotoxin-induced injury (FIG. 17). At 4 days post-injury, the cross-sectional area of muscle myofibers in wild-type mice was found to be only 13% larger compared to α7 integrin deficient muscle (FIG. 17). By days 10 and 28 post-cardiotoxin injury, the cross-sectional area of myofibers in α7 integrin null muscle was similar to wild-type animals (FIG. 17). Together these data indicate treatment with laminin-111 restored muscle repair and myofiber size in α7 integrin null muscle.

Figure 18:
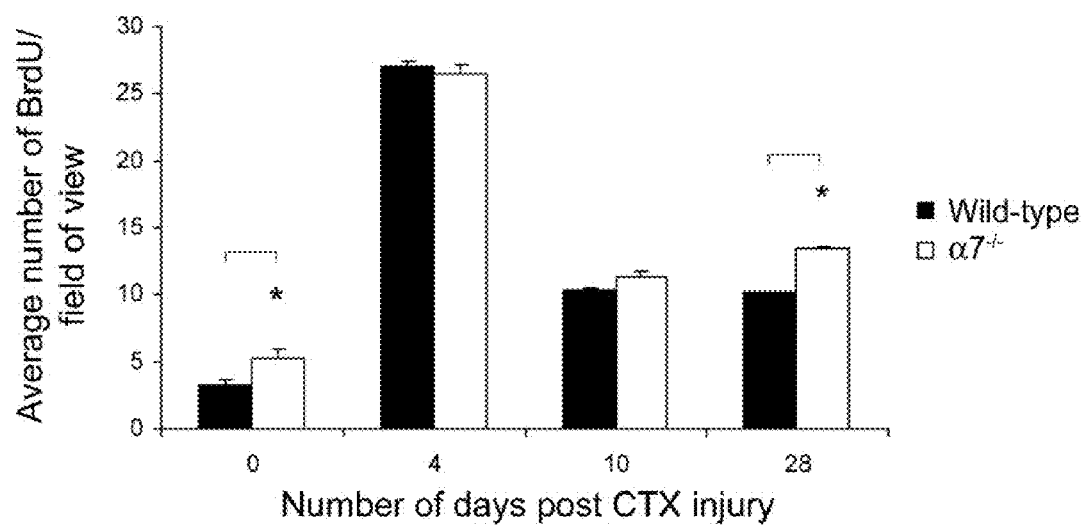
FIG. 18 provides a graph illustrating BrdU incorporation into wild-type and α7 integrin null mice treated with laminin-1.

Laminin Promotes Satellite Cell Proliferation in α7 Integrin Null Injured Muscle To examine if laminin treatment improved satellite cell proliferation, BrdU incorporation after muscle injury was measured (FIG. 18). At 0, 4 and 10 days post-cardiotoxin injury, no difference was observed in the number of BrdU positive satellite cells in wild-type and α7 integrin null muscle (FIG. 18). At 28 days post-injury, there were significantly more BrdU positive satellite cells in α7 integrin muscle compared wild-type (FIG. 18). These results indicate treatment with laminin restored satellite cell proliferation to wild-type levels.

Laminin Treatment Restores Myoblast Differentiation to α7 Integrin Null Muscle

Figure 19:
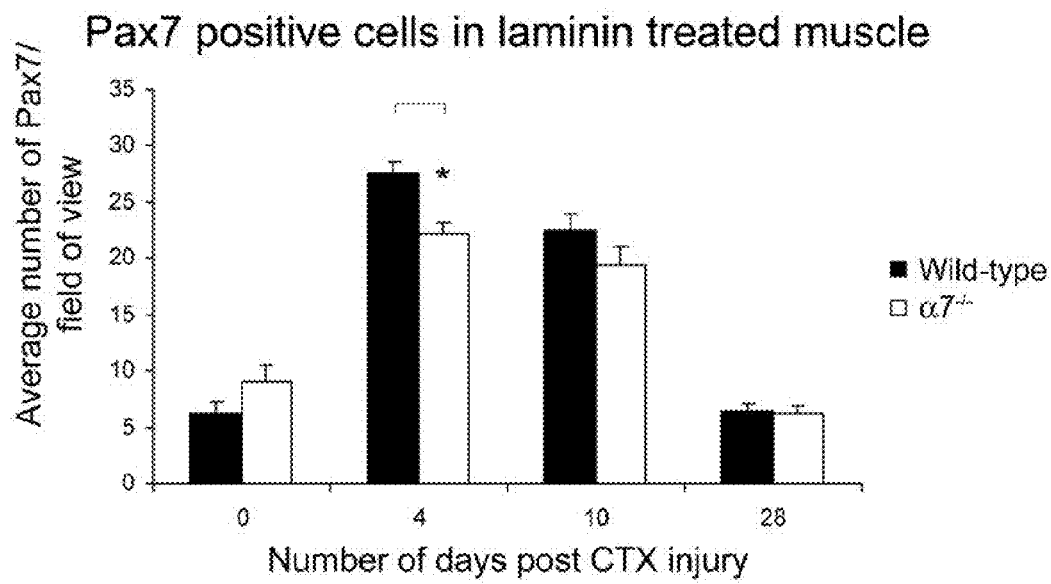
FIG. 19 provides a graph illustrating Pax7 expression in wild-type and α7 integrin null mice treated with integrin.
Figure 20:
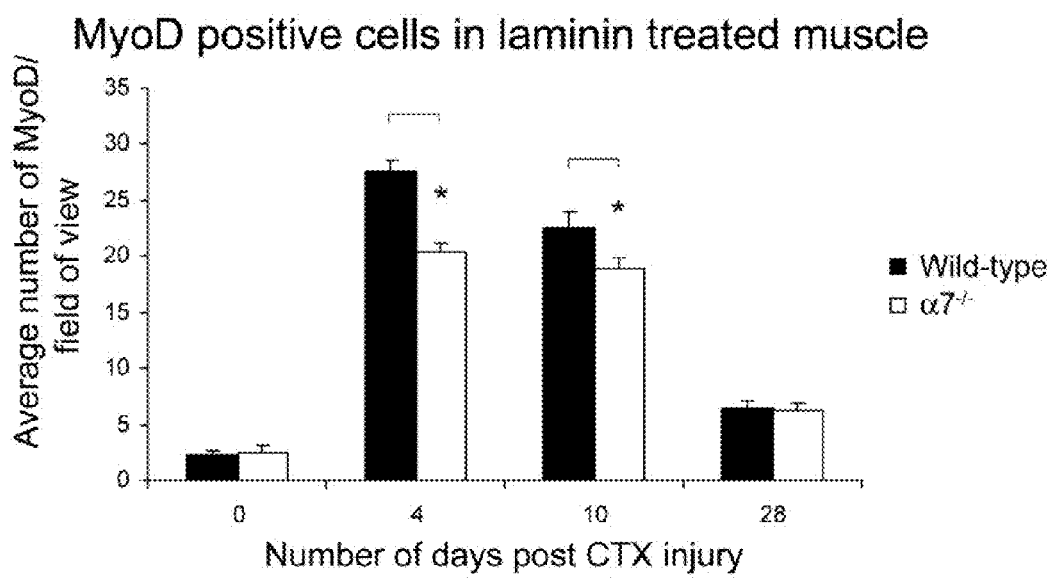
FIG. 20 provides a graph illustrating MyoD expression in wild-type and α7 integrin null mice treated with laminin.

To examine if treatment with laminin-1 μl restored the myogenic repair program in α7 integrin null muscle, expression of Pax7 and MyoD was examined (FIGS. 19 & 20). Prior to cardiotoxin-injury, wild-type and α7 integrin-null muscle exhibit a few Pax7 positive cells, which could be attributed to the minor damage from the laminin injection (FIG. 19). At 4 days post-cardiotoxin injury, there were 20% fewer Pax7 positive cells in laminin-treated α7 integrin null muscle compared to wild-type (FIG. 19). At 10 and 28 days post-cardiotoxin injury levels of Pax7 positive cells in the α7 integrin null muscle were similar to wild-type muscle (FIG. 19).

Analysis of MyoD revealed a few positive cells in laminin-treated wild-type and α7 integrin null TA muscle at day 0 (FIG. 20). At days 4 and 10 post-cardiotoxin injury, the number of MyoD positive cells in laminin-treated α7 integrin null muscle was approximately 20-25% lower than wild-type (FIG. 20). However by day 28, both wild-type and α7 integrin null muscle had similar numbers of MyoD positive cells (FIG. 20). These data indicate that laminin treatment substantially restored the number of myogenic cells and promoted activation of the myogenic program involved in muscle repair in α7 integrin null muscle.

Discussion

This Example demonstrates that α7 integrin null mice exhibit defective skeletal muscle regeneration after cardiotoxin-induced injury. Treatment with laminin corrected the defective repair phenotype. Although some aspects of the myogenic developmental program have been elucidated during skeletal muscle regeneration, the mechanisms by which the extracellular matrix and integrin cell surface receptors participate in myogenic repair are generally not well understood.

Muscle damage is followed by the rapid activation of satellite cells. Upon activation, these cells proliferate and activate myogenic developmental programs to repair damaged muscle. Models suggest a subpopulation of satellite cells remain as stem cells to replace cells that have progressed down the myogenic lineage pathway. During activation satellite cells express the transcription factors Pax3, Pax7, MyoD, myogenin and MRF4.

This Example demonstrates that loss of the α7 integrin leads to reduced satellite cell proliferation as determined by reduced BrdU incorporation and Pax7 expression in cardiotoxin-treated α7 integrin null muscle. In addition, myoblast differentiation was significantly reduced in injured α7 integrin deficient muscle as measured by MyoD expression. These data indicate the α7β1 integrin regulates a key transition early in muscle regeneration in which satellite cells are activated to proliferate and differentiate into myogenic cells capable of repairing muscle.

Results presented in this Example demonstrate a significant reduction in the presence of centrally located nuclei and delay in the expression eMyHC in injured α7 integrin null myofibers. The presence of centrally located nuclei and expression of eMyHC suggest that α7 integrin deficient myoblasts are capable of fusion in vivo. These observations support in vitro studies which demonstrate primary α7 integrin null myoblasts can fuse to form myotubes in cell culture. Together these observations suggest the delay in muscle repair in vivo is primarily due to defects in myoblast proliferation and differentiation leading to fewer myogenic cells capable of repairing damaged muscle.

Since the regenerative capacity of skeletal muscle is dependant on an intricate interplay between satellite cells and the extracellular matrix, absence of the α7 integrin may result in loss of an optimal laminin-rich microenvironment required for myogenic repair. To determine if decreased laminin deposition contributes to the reduced muscle regenerative phenotype observed in α7 integrin null mice, laminin-111 was injected into the muscle of mice prior to injury. Laminin is normally produced by skeletal muscle cells and secreted into the surrounding basal lamina. Interestingly, within 48-72 hours injected laminin-111 protein spread throughout the entire TA muscle and persisted for more than 31 days in the basal lamina. Injection of muscle with laminin-111 protein prior to cardiotoxin-induced injury restored muscle regeneration in α7 integrin null mice to wild-type levels. These data demonstrate that loss of the laminin microenvironment in α7 integrin-deficient skeletal muscle is the underlying cause of the defect in muscle repair observed in these animals.

While laminin-211 and laminin-221 are expressed in adult muscle, laminin-111 is only present in embryonic skeletal muscle. One possible explanation for the improved muscle regeneration in laminin-treated α7 integrin null muscle is that injection of laminin-111 may recapitulate an embryonic myogenic program in adult skeletal muscle. Activation of this embryonic program may result in enhanced myoblast activation and proliferation and improved muscle repair. However injection of laminin-111 into wild-type skeletal muscle did not increase regenerative capacity suggesting laminin-111 acted to replace laminin-211/221 in α7 integrin deficient skeletal muscle. These results suggest other laminin receptors are expressed in satellite cells that normally interact with laminin to promote myogenic repair or can act to compensate for the loss of α7 integrin in myoblasts.

This Example suggests that subjects with α7 integrin mutations suffer from congenital myopathy as a result of reduced muscle regenerative capacity due to reduced laminin-211/221 deposition. These data also demonstrate that direct injection of purified laminin-111 protein may serve as a potential therapy for patients with α7 integrin-congenital myopathy. Since loss of regenerative capacity has been implicated in a variety of muscular dystrophies including MDC 1A and DMD, laminin-111 protein therapy may be beneficial in other forms of muscular dystrophy.

EXAMPLE 2

Materials and Methods

Animals

C57BL/10ScSn (wild-type) and C57BL/10ScSn-Dmdmdx/J (mdx) strains of mice (Jackson Laboratories, Bar Harbor, Me.) were used in these studies in accordance with an animal protocol approved by the University of Nevada, Reno Animal Care and Use Committee.

Isolation of α7βgal$^{-/-}$ Myoblasts

The gastrocnemius muscles were removed from 10-day-old α7βgal$^{+/-}$ mice and tissue minced with scissors. Cells were enzymatically dissociated with 1.25 mg/ml collagen type II (Worthington Biochemical Corporation, Lakewood, N.J.) for 1 h at 37° C. The slurry was gently triturated and filtered through nylon mesh. Cells were separated from muscle fiber fragments by differential centrifugation and plated onto 100 mm tissue culture plates. Myoblasts were maintained in proliferation medium (Dulbecco's modified Eagle's medium (DMEM) supplemented with 10% fetal bovine serum (FBS), 0.5% chick embryo extract, 1% L-glutamine and 1% penicillin/streptomycin).

β-Galactosidase Staining

Myoblasts or myotubes were fixed in 4% paraformaldehyde for 5 minutes, washed with 1×PBS and permeabilized with a sodium deoxycholate/NP40 mixture for 30 minutes. X-gal (50 mM potassium ferrocyanide, 50 mM potassium ferricyanide, 1 M $MgCl_2$, and 100 mg/ml X-gal) was added to the plates and incubated at 37° C. for 2 hours. Plates were washed in PBS. Images were captured with a dissecting microscope and Spot digital camera.

Fluorescence Activated Flow Sorting (FACS)

Approximately $1\times10^6$ α7βgal$^{+/-}$ myoblasts were seeded on 100 mm cell culture plates coated with 0.1% gelatin and incubated overnight at 37° C. Growth media was removed and cells were treated for 16-24 hours with 100 nM LAM-111 in PBS. Cells were trypsinized, counted, pelleted and 30 µl DMEM containing 20% FBS growth medium added. 30 µl of 200 nM of FDG (Molecular Probes, Eugene, Oreg.) was added to the cells and incubated at 37° C. for 1 minute. To stop the reaction 600 µl of ice cold growth media was added to each sample and incubated on ice for 20 minutes. Samples were run on the Beckman Coulter XL/MCI flow cytometer and analyzed using FlowJo software.

Laminin-111 Injections

Natural mouse laminin (Invitrogen) at 100 nM in PBS was injected into the left tibialis anterior (TA) muscle of 10 day mdx mice. The contralateral right TA muscle was injected with PBS and served as a control. Mice were sacrificed and muscle was harvested at 5 weeks of age. For systemic delivery 1 mg/kg of laminin-111 in PBS was injected intraperitoneally at 10 days and tissues harvested for analysis at 5 weeks of age. Control mdx mice were injected with the same volume of PBS.

Evan's Blue Dye Uptake

Mice were injected intraperitoneally with 50 µl per 10 g of body weight with sterile Evans blue dye solution (10 mg/ml). After 3 hours, the TA muscle was harvested and flash-frozen in liquid nitrogen. 10 Mm cryosections were placed on microscope slides and fixed in 4% paraformaldehyde. To outline muscle fibers, tissue sections were incubated with 2 µg/ml Oregon Green-488 conjugated wheat germ agglutinin (WGA) (Molecular Probes, Eugene, Oreg.). A minimum of 1000 fibers per animal were counted to determine the percentage of muscle fibers positive for Evans blue dye uptake. At least five animals from each genotype were analyzed. Images were captured and counted at 630× magnification.

Blood Chemistry

Blood was collected at 5 weeks of age and allowed to clot at room temperature for a minimum of 30 minutes. After centrifugation at 3000 rpm, serum was collected. Serum was sent to Comparative Pathology Laboratory at the University of California, Davis to assay for creatine kinase, creatine and blood urea nitrogen (BUN).

Immunofluorescence

Tissues were embedded in Tissue-TEK Optimal Cutting Temperature compound (Sakura Finetek USA Inc., Torrance, Calif.). Using a Leica CM1850 cryostat (Leica Microsystems, Wetzlar, Del.), 10-micron sections were placed onto Surgipath microscope slides (Surgipath Medical Industries, Richmond, Ill.). The α7 integrin was detected with a 1:1000 dilution of anti-CA5.5 rat monoclonal antibody (Sierra Biosource, Morgan Hill, Calif.) followed by a 1:1000 dilution of FITC-conjugated anti-rat secondary antibody. The β1D integrin was detected with a 1:500 dilution of rabbit polyclonal antibody followed by a 1:500 dilution of FITC-conjugated anti-rabbit antibody. Laminin-α1 was detected with a 1:500 dilution of MAB1903 (Chemicon International, Temecula, Calif.). Dystrophin was detected with the mouse monoclonal Dys2 antibody (Novacastra Laboratories, Ltd, Newcastle upon Tyne, UK) and utrophin was detected with MANCHO7 7F3 monoclonal antibody against utrophin (Glenn Morris, Center for Inherited Neuromuscular Disease, Shropshire, UK) at a dilution of 1:200. The mouse monoclonal antibodies were used in conjunction with a mouse-on-mouse (MOM) immunodetection kit (Vector Laboratories, Burlingame, Calif.) to block mouse immunoglobulin and a 1:500 dilution of FITC-conjugated anti-mouse secondary antibody. Acetylcholine receptors were detected with Rhodamine-labeled α-bungarotoxin at 1:1000 (Molecular Probes, Eugene, Oreg.). Fluorescence was observed with a Zeiss Axioskop 2 Plus fluorescent microscope and images were captured with Zeiss AxioCam HRc digital camera and Axiovision 4.1 software (all available from Carl Zeiss MicroImaging, Thornwood, N.Y.).

Histology

Tissue sections were fixed in ice-cold 95% ethanol for 2 minutes followed by 70% ethanol for 2 minutes and then re-hydrated in running water for 5 minutes. The sections were stained with Gill's hematoxylin (Fisher Scientific, Fair Lawn, N.J.) and rinsed in water for 5 minutes. Sections were placed in Scott's solution (0.024 M $NaHCO_3$, 0.17 M $MgSO_4$) for 3 minutes and rinsed in water for 5 minutes. Sections were then stained with eosin (Sigma-Aldrich, St Louis, Mo.) for 2 minutes. Sections were progressively dehydrated in ice-cold 70% and 95% ethanol for 30 seconds each, followed by 100% ethanol for 2 minutes and cleared in xylene for 5 minutes prior to mounting with DePeX mounting medium (Electron Microscopy Sciences, Washington, Pa.). Central myonuclei in regenerating muscles were counted at 630× magnification by bright-field microscopy. The number of central nuclei per muscle fiber was determined by counting a minimum of 1000 muscle fibers per animal. At least five animals from each genotype were analyzed.

Immunoblotting

To analyze α7 integrin, protein was extracted using 200 mM octyl-β-D-glucopyranoside (Sigma Aldrich, St Louis, Mo.), 50 mM Tris-HCl pH 7.4, 150 mM NaCl, 1 mM $CaCl_2$, 1 mM $MgCl_2$, 2 mM PMSF and a 1:200 dilution of Protease Inhibitor Cocktail Set III (Calbiochem, EMD Biosciences, San Diego, Calif.). Lysate was collected and centrifuged for 15 minutes at 10,000×g, and supernatant was transferred to a fresh tube. Protein was quantified by Bradford assay and 40 μg of total protein was separated on 7.5% SDS-PAGE gels under non-reduced conditions, and transferred to nitrocellulose membranes. Membranes were blocked in Odyssey Blocking Buffer (LiCor Biosciences, Lincoln, Nebr.) that was diluted 1:1 in phosphate-buffered saline (PBS). The α7 integrin was detected with a 1:500 dilution of rabbit anti-α7B (B2 347) polyclonal antibody. Blots were incubated with a 1:5000 dilution of Alexa Fluor 680-coupled goat anti-rabbit IgG (Molecular Probes, Eugene, Oreg.) to detect the primary antibody.

To examine utrophin expression, protein was extracted from the PBS and LAM-111 injected mdx and wild-type tibialis anterior muscle with RIPA buffer (50 mM Hepes pH 7.4, 150 mM NaCl, 1 mM $Na_3VO_4$, 10 mM NaF, 0.5% Triton X-100, 0.5% NP40, 10% glycerol, 2 mM PMSF and a 1:200 dilution of Protease Inhibitor Cocktail Set III) and quantified by Bradford assay (BioRad Laboratories Inc., Hercules, Calif.). 80 μg of total protein were separated on a 7.5% SDS-PAGE gel and transferred to nitrocellulose membrane. The blot was incubated with a 1:200 dilution of anti-utrophin mouse monoclonal antibody (MANCHO3 8A4, a kind gift of Glenn Morris, Center for Inherited Neuromuscular Disease, Shropshire, UK) followed by a 1:50,000 dilution of horseradish peroxidase (HRP)-labeled goat anti-mouse secondary antibody. The 395 kDa utrophin band was detected by chemiluminescence and normalized for protein loading by probing the same blot with anti-Cox-1 antibody (Santa Cruz Biotechnology, Santa Cruz, Calif.). Band intensities were quantified by using ImageQuant TL software (Amersham Biosciences, Piscataway, N.J.).

Statistical Analysis

All averaged data are reported as the mean±standard deviation. Comparisons between multiple groups were performed by one-way-analysis of variance (ANOVA) for parametric data or by Kruskal-Wallis one-way-analysis of variance on ranks for non-parametric data using SigmaStat 1.0 software (Jandel Corporation, San Rafael, Calif.). $P<0.05$ was considered statistically significant.

Discussion

Duchenne Muscular Dystrophy (DMD) is a devastating neuromuscular disease caused by mutations in the gene encoding dystrophin. The α7β1 integrin and utrophin are laminin binding proteins up-regulated in the muscle of DMD patients and in the mdx mouse model. Transgenic over-expression of utrophin or α7 integrin in dystrophic mice alleviates muscle disease making these genes targets for pharmacological intervention. To determine whether laminin regulates α7 integrin expression, cultured mouse and human myoblasts were treated with laminin and assayed for α7 integrin expression. This Example demonstrates that laminin-111, a form of laminin highly expressed during embryonic development, increased α7 integrin expression in cultured myoblasts from mice and DMD patients. Intramuscular injection of laminin-111 into mdx mice increased β7 integrin and utrophin expression, stabilized the sarcolemma and prevented muscle pathology. Systemic laminin-111 protein therapy restored serum creatine kinase levels in mdx mice to the normal range. These findings demonstrate laminin-111 is a highly potent and novel protein therapeutic for the mouse model of DMD and represents a novel paradigm for the systemic delivery of extracellular matrix proteins as a therapy for genetic diseases.

Duchenne Muscular Dystrophy (DMD) is the most common X-linked disease affecting 1 in 3,500 male births. DMD patients exhibit severe and progressive muscle wasting with symptoms first detected at 2 to 5 years of age. As the disease progresses, patients are confined to wheelchairs, require ventilator assistance and die in their second or third decade of life. To date there is no effective treatment or cure for this devastating neuromuscular disease.

DMD patients and mdx mice (the mouse model for DMD) have mutations in the gene encoding dystrophinm, resulting in a loss of dystrophin protein. Dystrophin is a 427 kDa protein located on the inner cytoplasmic membrane of muscle fibers. Through its N-terminal rod domain repeats, dystrophin interacts with F-actin of the cell cytoskeleton. The C-terminal region of dystrophin interacts with a transmembrane complex composed of α- and β-dystroglycans, dystrobrevins, α- and β-syntrophins and sarcoglycans. The dystrophin glycoprotein complex provides a transmembrane linkage between the cell cytoskeleton and laminin in the extracellular matrix of muscle. Loss of dystrophin results in a failure of this critical laminin-binding complex to form, leading to damage and progressive muscle weakness.

In the absence of dystrophin, two additional laminin-binding complexes, the α7β1 integrin and utrophin glycoprotein complexes, are up-regulated in the skeletal muscle of DMD patients and mdx mice. Transgenic enhancement of utrophin or α7 integrin in skeletal muscle alleviates muscle disease in dystrophic mice. On the other hand, loss of utrophin or α7 integrin in mdx mice results in more severe phenotypes and reduced viability. Together these results indicate that utrophin and the α7β1 integrin are genetic modifiers of disease progression and targets for drug-based therapies that boost their expression.

Figure 21:
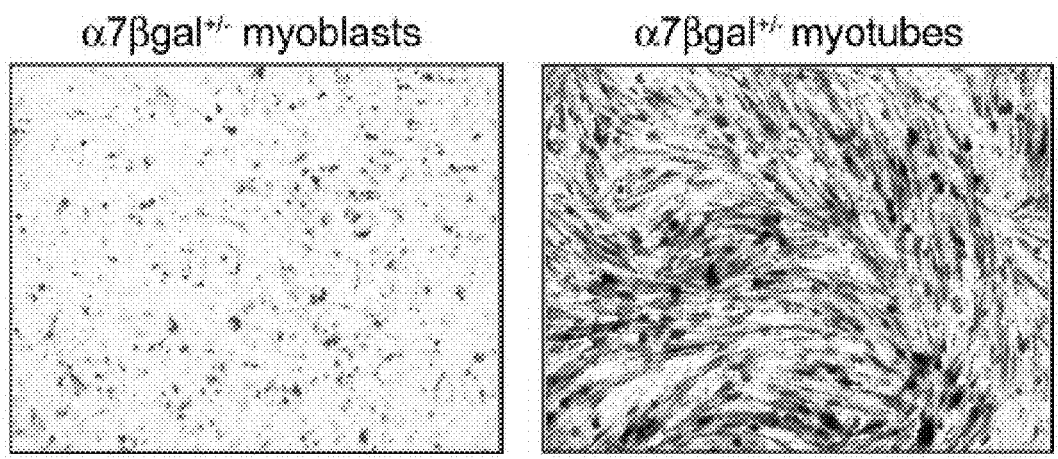
FIG. 21 is an image of X-gal staining demonstrating that α762 gal$^{+/-}$ myoblasts express β-galactosidase (left panel) which increases upon differentiation to myotubes (right panel).
Figure 22:
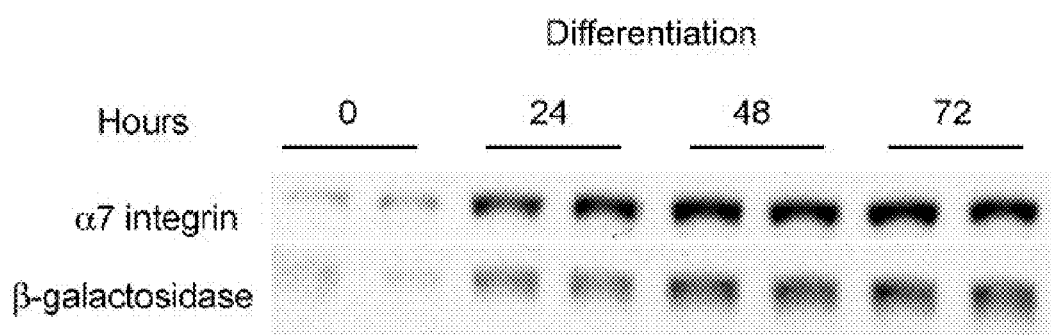
FIG. 22 is an image of a Western analysis of α7 integrin and β-galactosidase expression in α7βgal$^{+/-}$ cells differentiated from 0-72 hours.

To whether particular molecules increase α7 integrin expression, a muscle cell based assay was developed. A α7 integrin null mouse was produced in which exon 1 of the gene encoding the α7 integrin was replaced by the LacZ reporter gene. In these mice, all the transcriptional regulatory elements are retained allowing α7 integrin promoter activity to be reported by β-galactosidase. Primary myoblasts (designated α7βgal$^{+/-}$) were isolated from 10 day old α7$^{+/-}$ pups. α7βgal$^{+/-}$ myoblasts expressed β-galactosidase which increased upon differentiation (FIGS. 21 and 22), consistent with the expression pattern of α7 integrin in myoblasts and myotubes. The activity of the α7 integrin promoter was measured by β-galactosidase cleavage of the non-fluorescent compound fluorescein di-β-D-galactopyranoside (FDG) to fluorescein.

Figure 23:
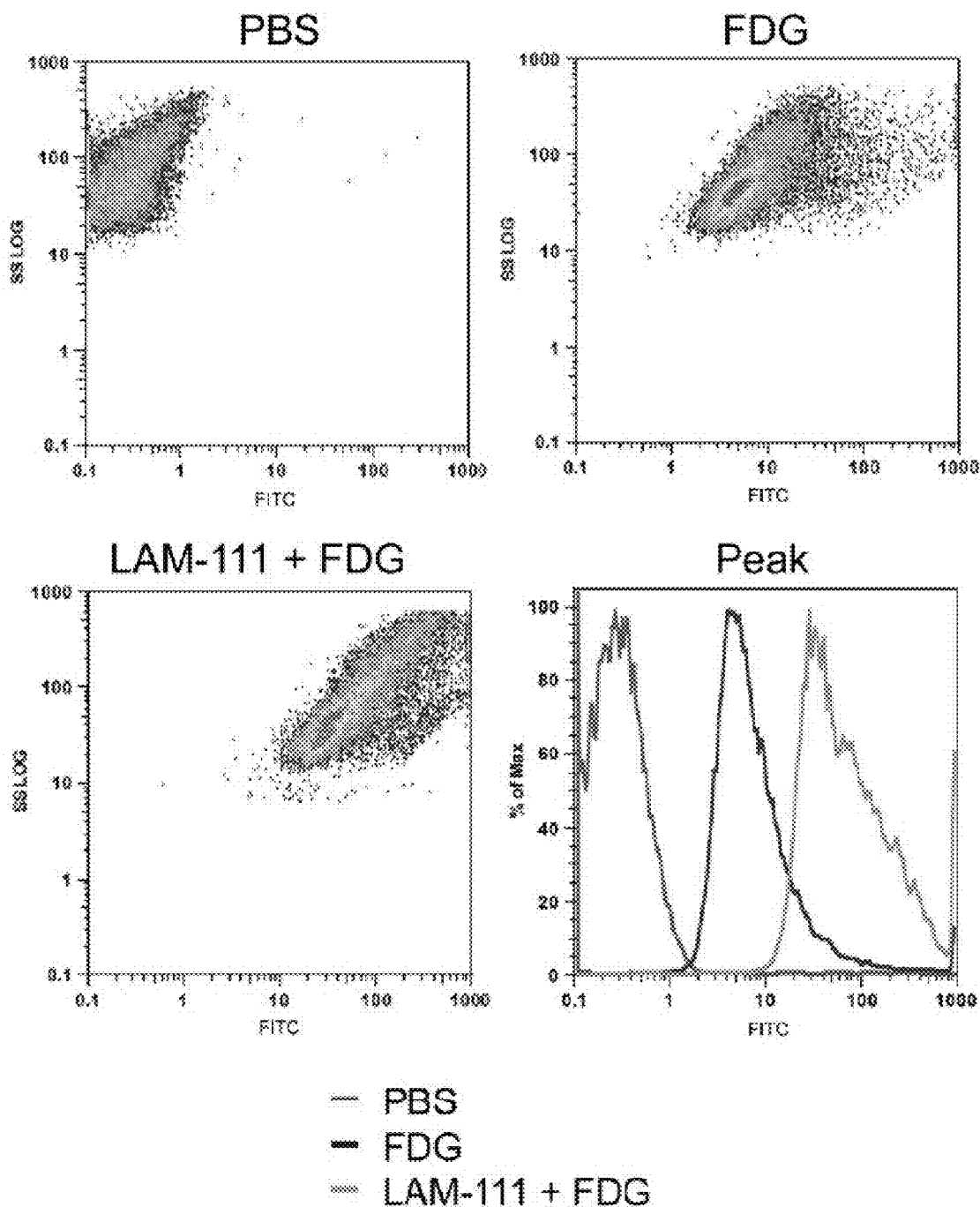
FIG. 23 is fluorescence-activated sorting (FACS) graphs (log of side scatter versus FITC staining (intensity)) demonstrating that α7βgal$^{+/-}$ myoblasts exhibit increased β-galactosidase expression following 100 nM LAM-111 treatment.
Figure 24:
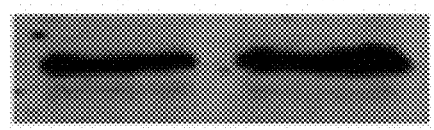
FIG. 24 is an image of a Western analysis of α7B integrin and Cox-1 expression in laminin-111- and phosphate-buffered saline-treated C2C12 and Duchenne muscular dystrophy myoblasts.
Figure 24:
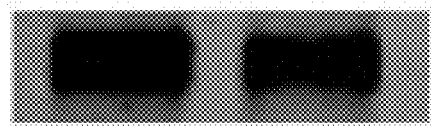
Figure 24:
Figure 24:
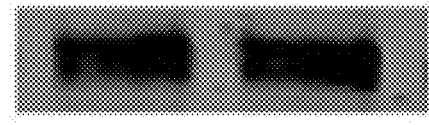
Figure 25:
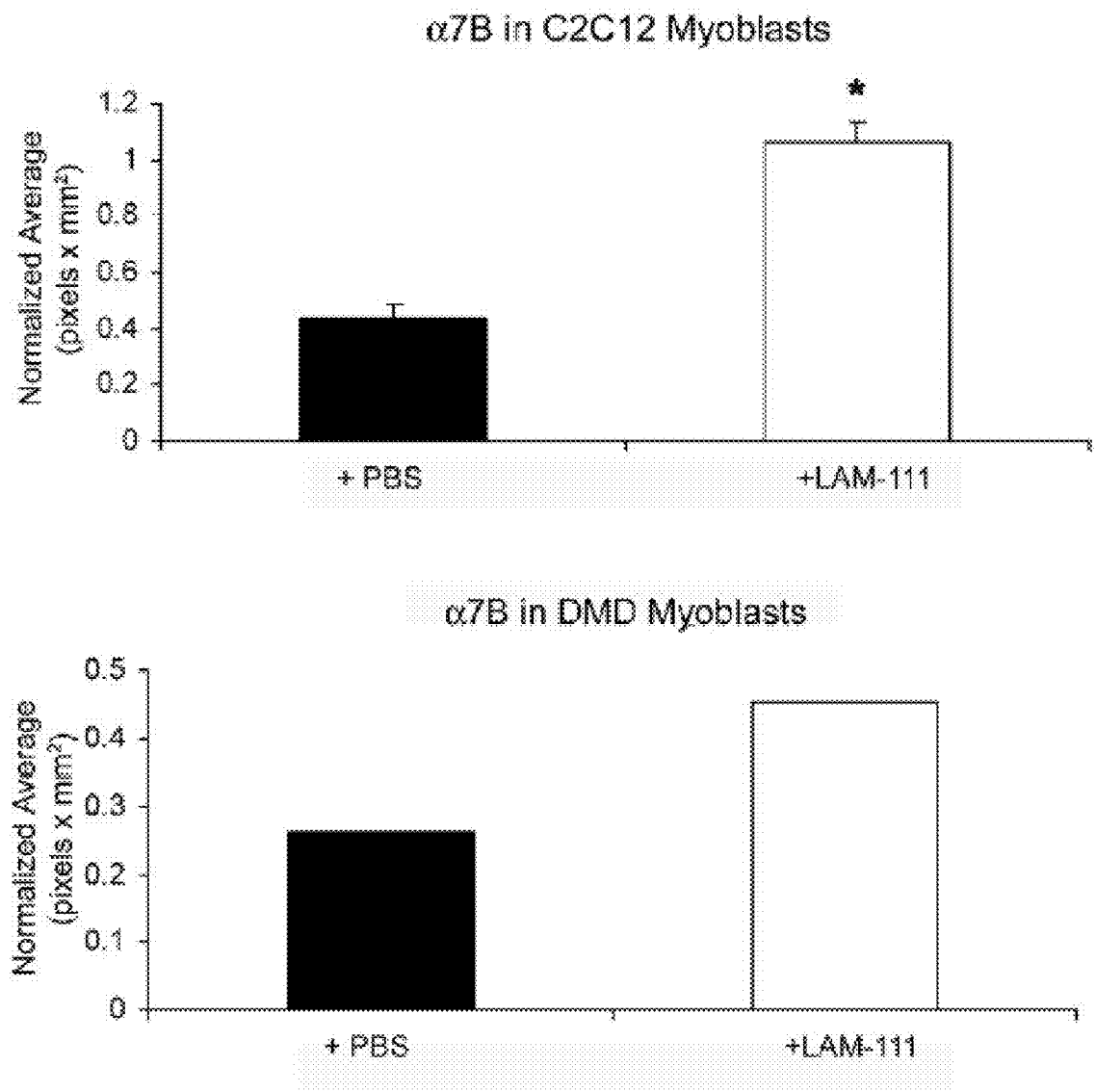
FIG. 25 provides a graph (pixels versus square millimeters) of α7B integrin expression in laminin-111- and phosphate-buffered saline-treated C2C12 and Duchenne muscular dystrophy myoblasts.

Several lines of evidence suggest positive feedback in the regulation of laminin and α7 integrin expression. Mutations in the gene encoding laminin-α2 result in congenital muscular dystrophy type 1A (MDC1A). Both MDC1A patients and laminin-α2 deficient mice have dramatically reduced levels of α7 integrin which may contribute to severe muscle pathology. In addition, laminin-α2 is decreased in α7 integrin null skeletal muscle. To determine the relationship between laminin and α7 integrin expression, α7βgal$^{+/-}$ myoblasts were exposed to various concentrations of laminin-111 from 0-200 nM for 24 hours. Studies suggest laminin-111 is functionally similar to laminin-211 and interacts with the α7β1 integrin. Fluorescence activated cell sorting (FACS) analysis revealed maximal α7 integrin promoter activity at 100 nM laminin-111 (FIG. 23).

α7 integrin protein in laminin-111 treated C2C12 mouse myoblasts and DMD primary myoblasts was quantified. Protein extracts from laminin-treated myoblasts were subjected to Western analysis to detect α7B integrin. Laminin-111 produced a 2-fold increase in α7B integrin in C2C12 and DMD myoblasts (FIGS. 24 and 25). These data indicate laminin-111 increases α7 integrin expression in human and mouse muscle cells.

Figure 26:
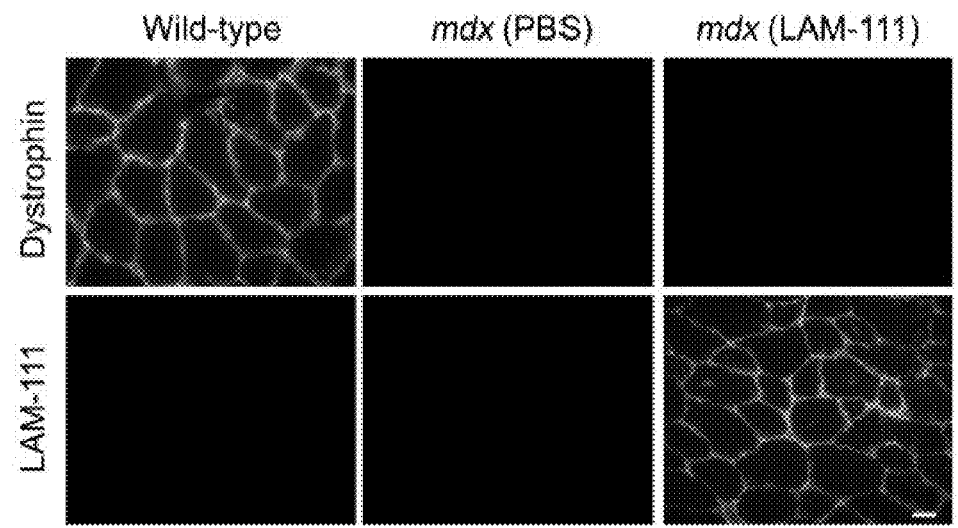
FIG. 26 is immunofluorescence images (scale bar=10 μm) of the tibialis anterior muscle of control, phosphate-buffered saline-treated, and laminin-111-treated muscle, illustrating the absence of dystrophin in mdx muscle treated with laminin-111 or phosphate-buffered saline and that, while wild-type and phosphate-buffered saline-injected mdx muscle lacked laminin-111, laminin-111 was detected in the extracellular matrix of laminin-111-injected mdx muscle.

It was then determined whether the above in vitro results with laminin-111 could be translated in vivo to increase α7 integrin expression in skeletal muscle. The left tibialis anterior (TA) muscles of 10 day old mdx mice were injected with 100 μl of 100 nM laminin-111, while the right TA muscle was injected with 100 μl PBS and served as the contralateral control. At 5 weeks of age mice were sacrificed and the TA muscles were harvested. Laminin-111 is not normally expressed in adult muscle and the injected protein was detected with an anti-laminin-α1 antibody. Immunofluorescence revealed the injected laminin-111 protein was deposited throughout the basal lamina of the TA muscle of 5 week old mdx mice (FIG. 26). The images also confirm that dystrophin was present in the wild type muscle, but absent in both the PBS and laminin-111 treated mdx muscle.

Figure 27:
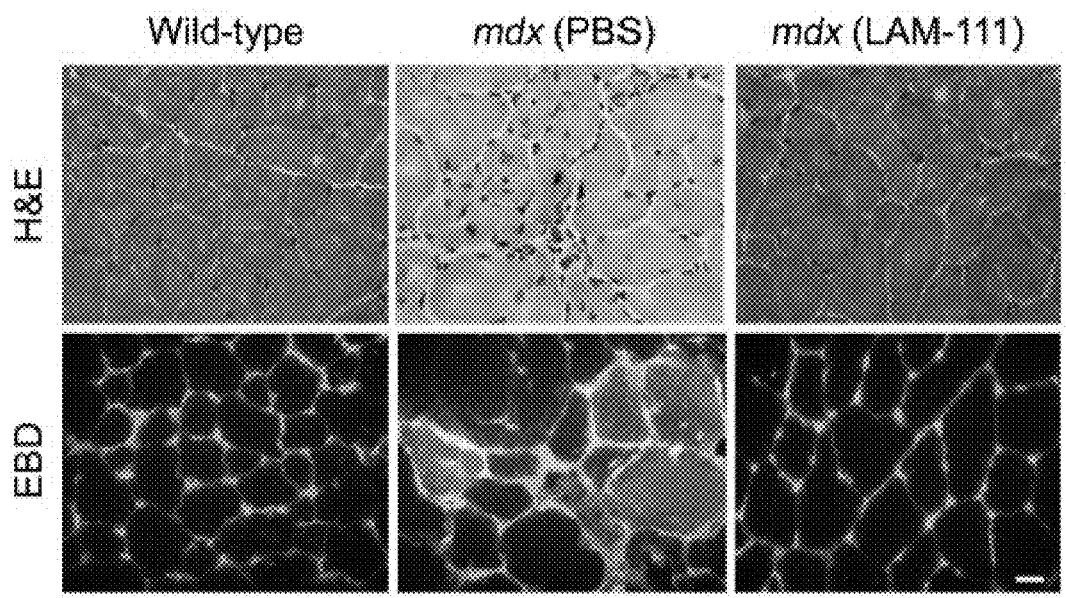
FIG. 27 is photomicrographs (scale bar=10 μm) of hematoxylin and eosin (top panels) staining and Evans blue dye (EBD) uptake (bottom panels) for wild-type, phosphate-buffered saline-injected mdx muscle, and laminin-111-injected mdx muscle, illustrating that laminin-111-injected muscle exhibited reduced centrally located nuclei and EBD uptake compared to phosphate-buffered saline-injected mdx muscle.
Figure 28:
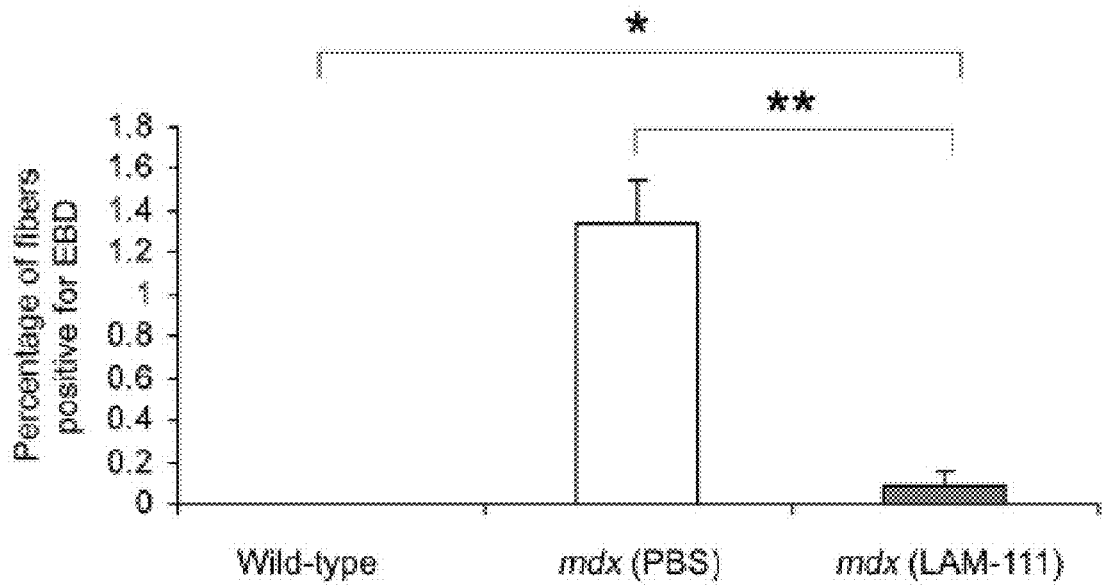
FIG. 28 provides graphs of Evans blue dye uptake (left graph, percentage of positive fibers) and centrally located nuclei (right graph, percentage of fibers positive for centrally located nuclei) for wild-type, mdx muscle injected with phosphate-buffered saline, and mdx muscle treated with laminin-111.
Figure 28:
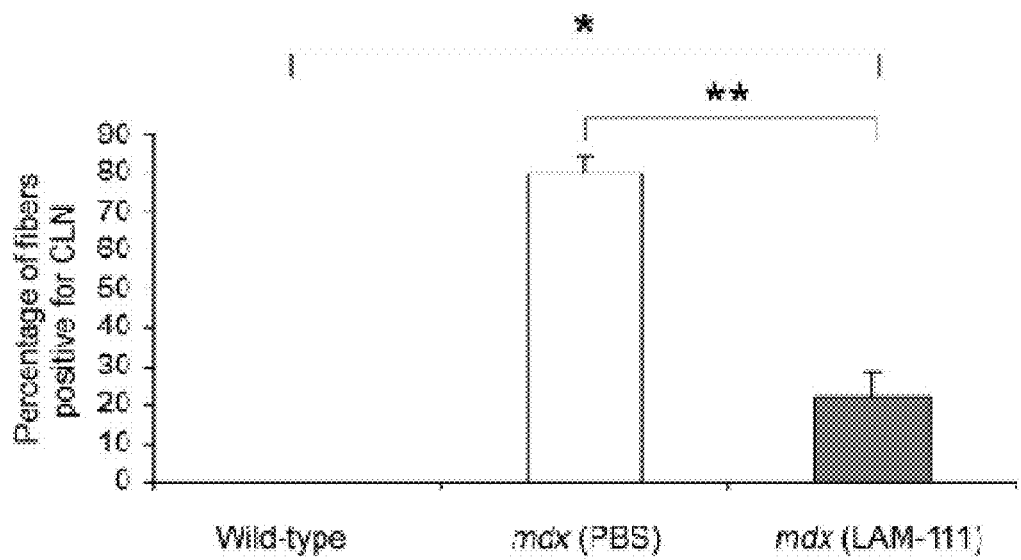

To determine if laminin-111 prevented muscle pathology in mdx mice, Evans blue dye (EBD) uptake and hemotoxylin and eosin (H&E) staining were performed on cryosections from PBS and laminin-111-injected TA muscle (FIG. 27). Analysis revealed that mdx muscles injected with laminin-111 had a 12-fold reduction in the percentage of fibers positive for EBD compared to the contralateral controls (FIG. 28, $*P<0.05$, $**P<0.001$, n=5 mice/group). In addition, mdx muscles injected with laminin-111 showed a 4-fold decrease in the percentage of muscle fibers with centrally located nuclei (FIG. 28, $*P<0.05$, $**P<0.001$, n=5 mice/group). These results indicate laminin-111 protein therapy dramatically increased sacrolemmal integrity and reduced the requirement for muscle repair.

Figure 29:
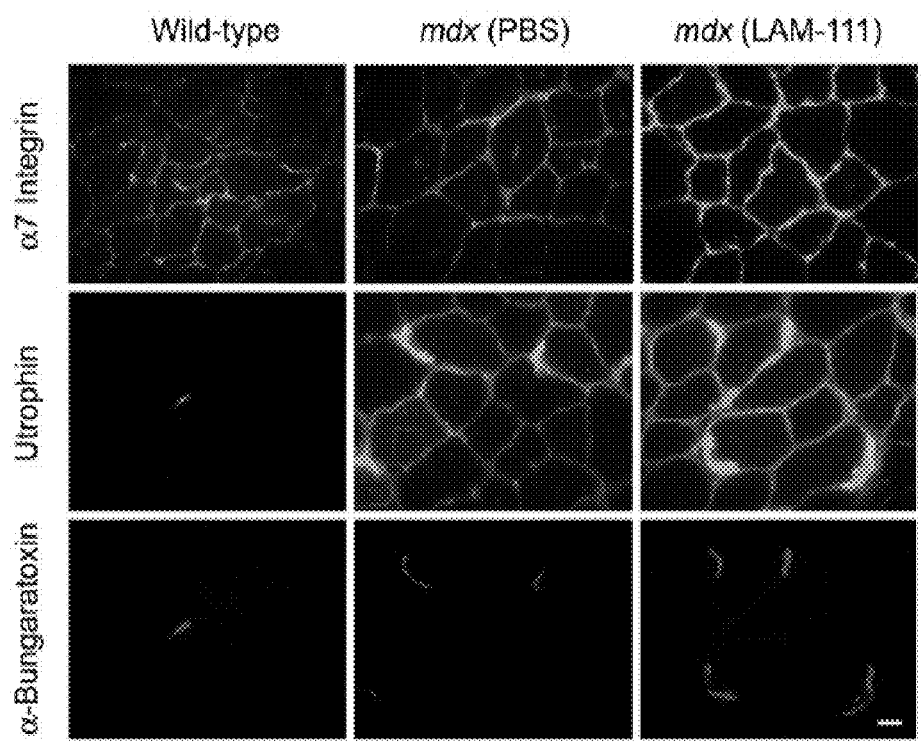
FIG. 29 is immunofluorescence images (scale bar=10 μm) of wild type muscle, phosphate-buffered saline-treated mdx muscle, and laminin-111-treated mdx muscle illustrating the presence or absence of α7 integrin, utrophin, and α-bungarotoxin.

To determine the mechanism by which laminin-111 protein therapy protected dystrophin-deficient muscle from damage, immunofluorescence analysis of utrophin and α7 integrin were done. Results revealed increased expression and extrajunctional localization of α7 integrin and utrophin in laminin-111-treated muscles of mdx mice compared to controls (FIG. 29).

Figure 30:
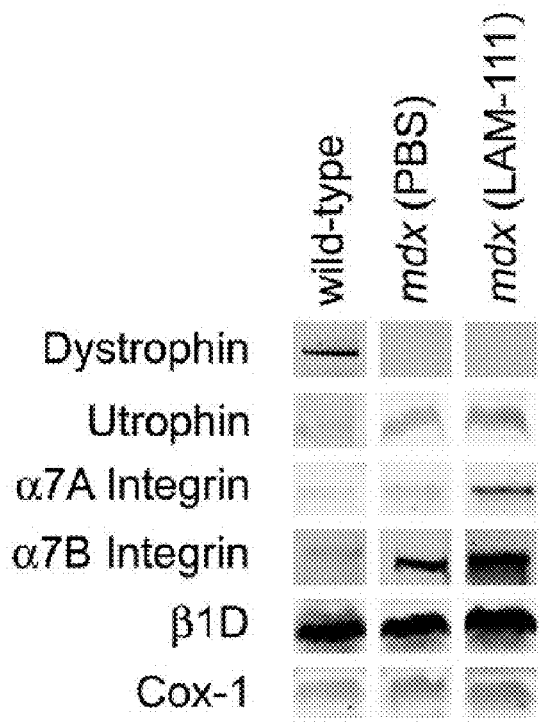
FIG. 30 is an image of a Western analysis of dystrophin, utrophin, α7A integrin, α7B integrin, β1D integrin, and Cox-1 expression in wild-type muscle, phosphate-buffered saline-treated mdx muscle, and laminin-111-treated mdx muscle.
Figure 31:
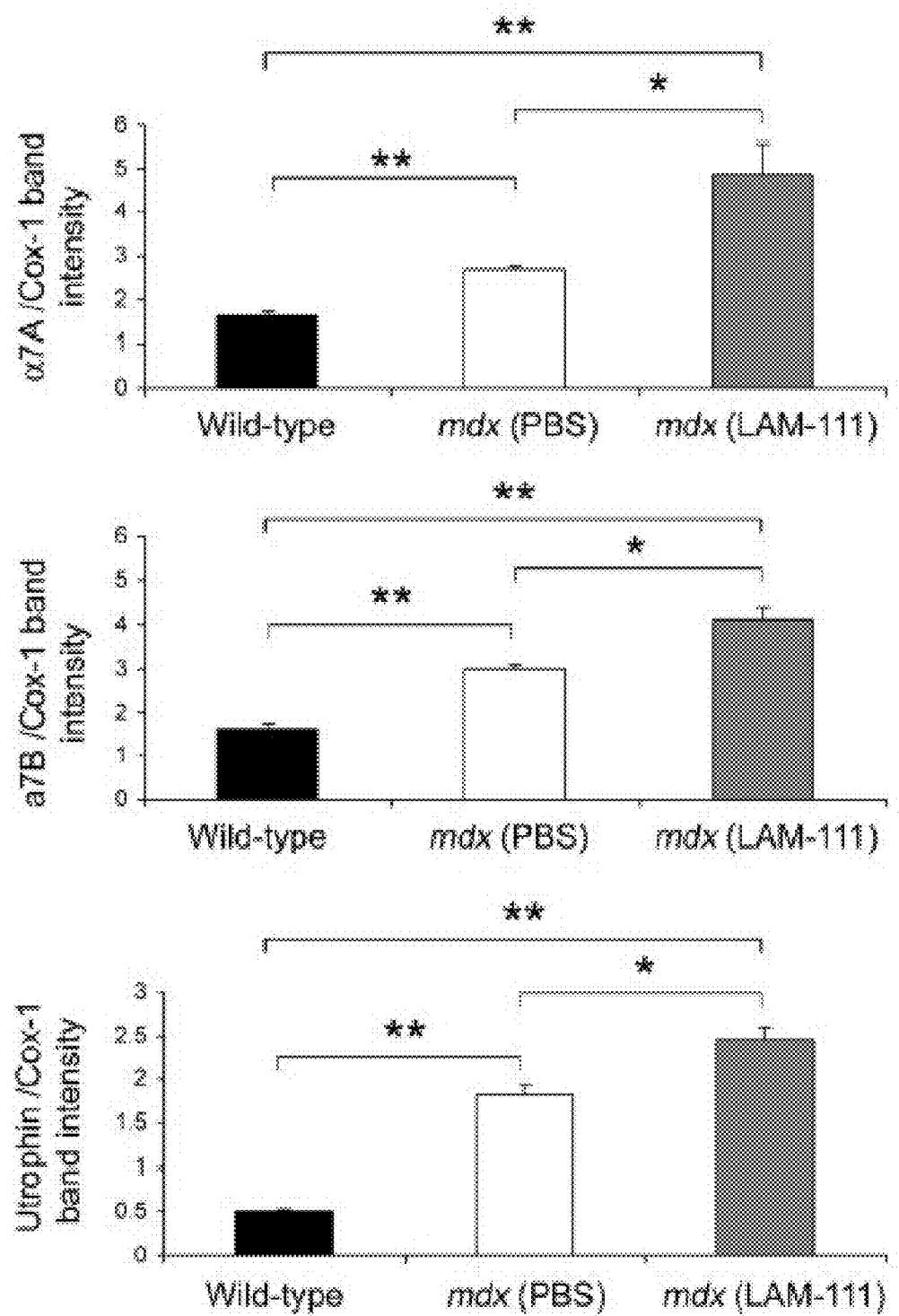
FIG. 31 provides graphs of the ratio of α7A integrin/Cox-1 (top graph), α7B integrin/Cox-1 (middle graph), and utrophin/Cox-1 (bottom graph) for wild-type muscle, phosphate-buffered saline-treated mdx muscle, and laminin-111-treated mdx muscle.

To confirm and quantify these observations, PBS and laminin-111-treated mdx muscles were subjected to Western analysis (FIG. 30). A 1.6- and 2.6-fold increase in α7A and α7B integrin isoforms respectively was observed in laminin-111 treated mdx muscles compared with controls (FIG. 31, $*P=<0.05$, $**P=<0.001$, n=5 mice/group). Protein loading was normalized to cyclooxygenase-1 (cox-1). In addition, a 1.3-fold increase in utrophin was observed in laminin-111-treated muscles (FIG. 31, $*P=<0.05$, $**P=<0.001$, n=5 mice/group). No significant change in β1D integrin levels was seen, consistent with results reported in α7 integrin transgenic mice. These results indicate that laminin-111 increased the expression of both α7 integrin and utrophin, two proteins known to alleviate muscle pathology when transgenically over-expressed in dystrophic muscle.

Figure 32:
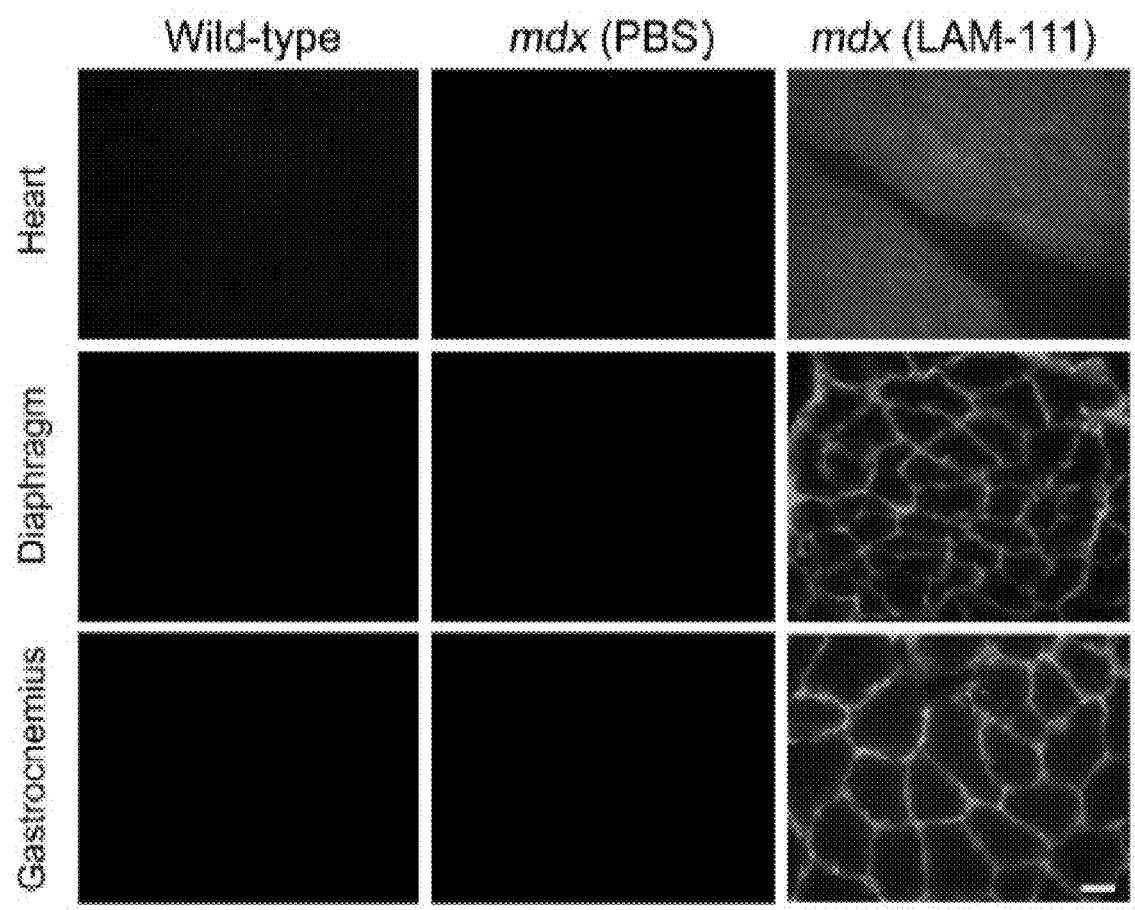
FIG. 32 is immunofluorescence images (scale bar=10 μm) of wild type muscle, phosphate-buffered saline-treated mdx muscle, and laminin-111-treated mdx muscle illustrating that a single 1 mg/kg dose of laminin-111 protein delivered intraperionteally in mdx mice resulted in localization to the heart, diaphragm and gastrocnemius.
Figure 33:
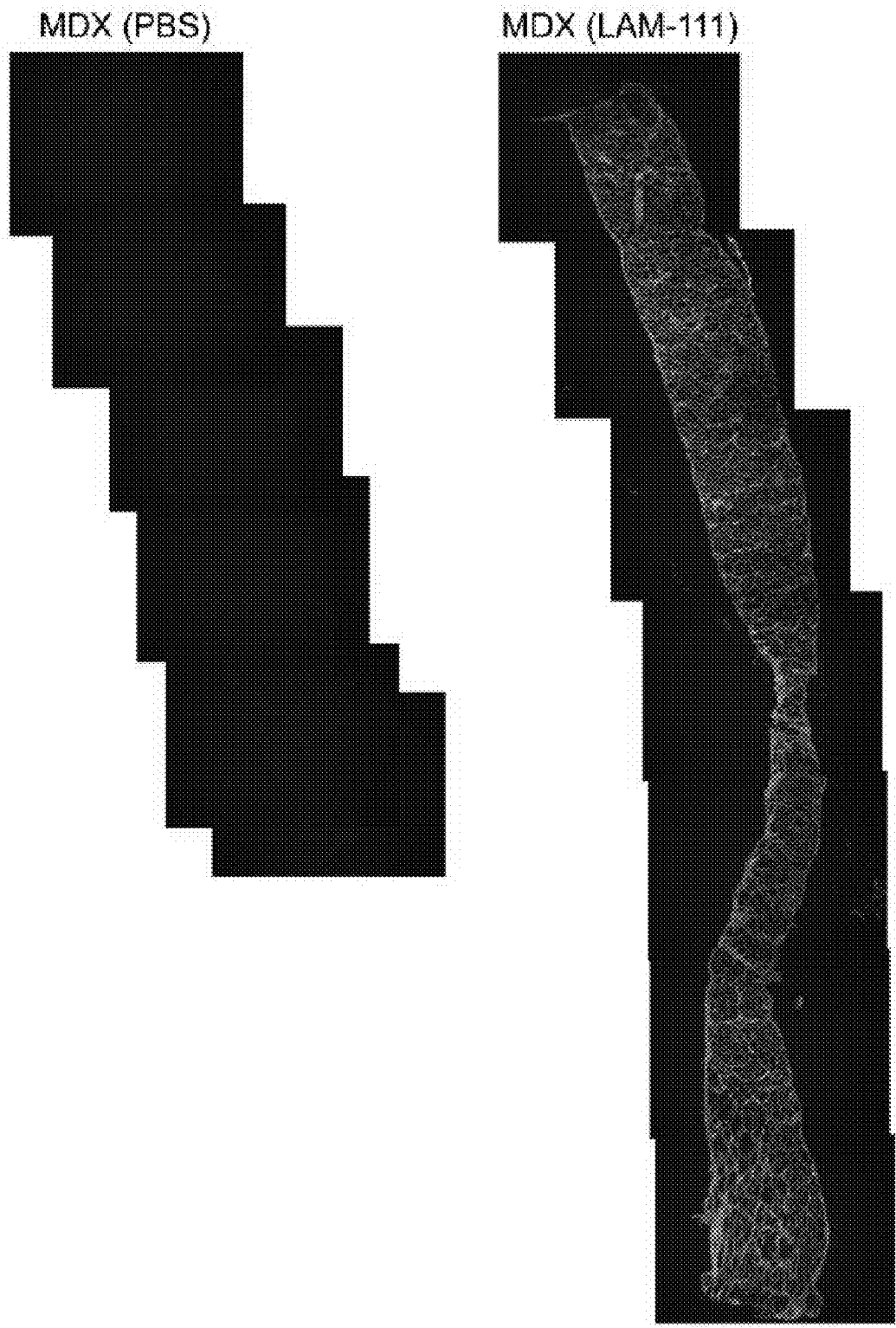
FIG. 33 is immunofluorescence images of the diaphragm of mdx mice treated with phosphate-buffered saline (left images) or laminin-111 (right images), illustrating that laminin-111 was located throughout the diaphragm of mdx mice following intraperitoneal injection with laminin-111.

DMD patients suffer from generalized muscle wasting. An effective therapy therefore should target all muscles, including the heart and diaphragm. It was then determined if laminin-111 protein could be delivered systemically to these muscles. Ten day-old mdx pups were injected intraperitoneally with one dose of laminin-111 at 1 mg/kg and tissues analyzed at 5 weeks of age. Immunofluorescence analysis revealed the presence of laminin-α1 throughout the basal lamina of diaphragm and gastrocnemius muscles of laminin-111 injected mice, while controls were negative (FIGS. 32 and 33). Analysis of cardiac muscle showed laminin-111 surrounding cardiomyocytes (FIG. 32).

Figure 34:
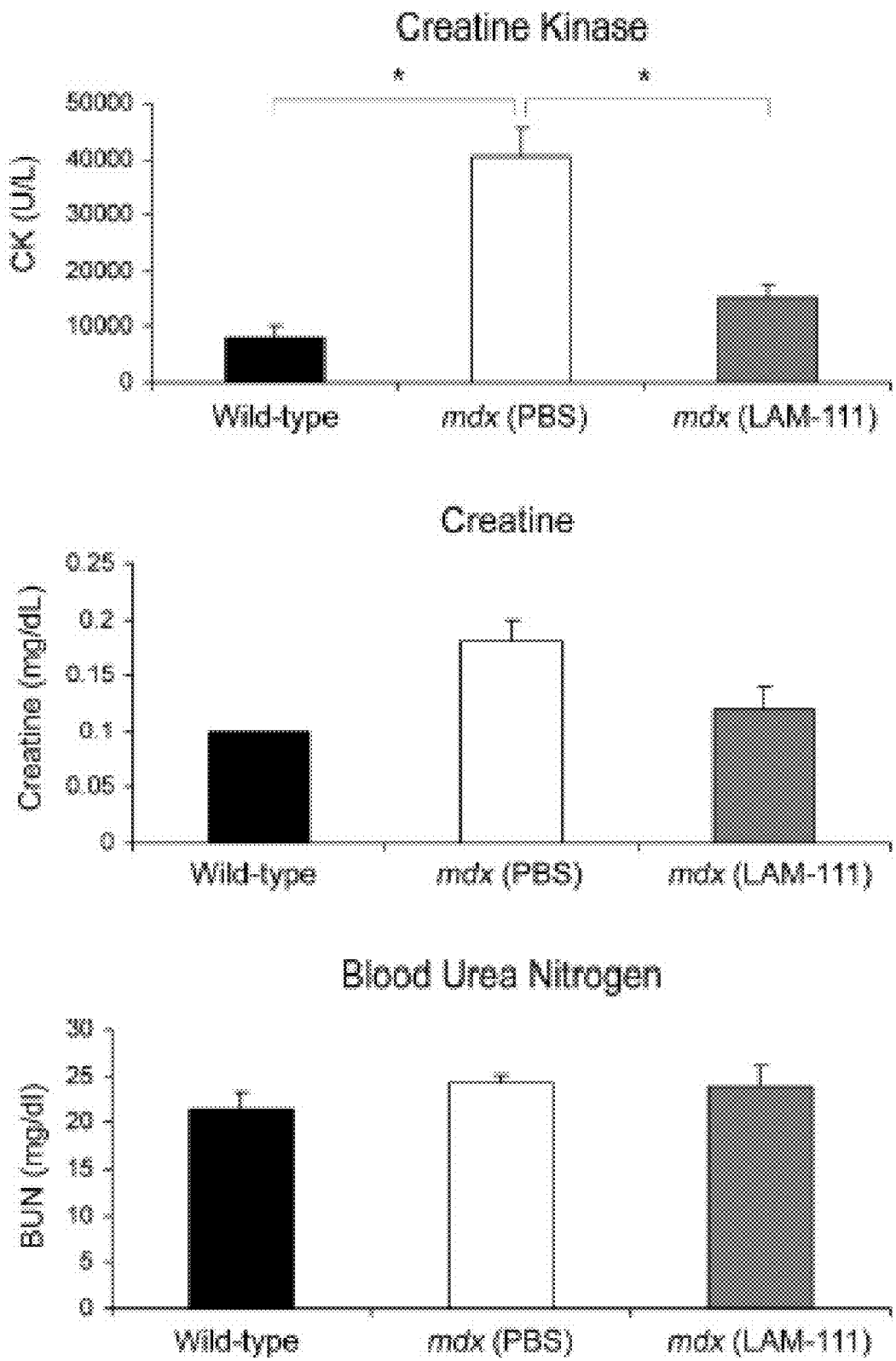
FIG. 34 provides graphs of creatine (mg/dl) and blood urea nitrogen (mg/dl) levels for wild-type muscle, mdx muscle injected with phosphate-buffered saline, and mdx muscle treated with laminin-111.

To determine if systemic delivery of laminin-111 was therapeutic, serum was collected 3 weeks after laminin-111 injections and creatine kinase levels measured. Serum creatine kinase is highly elevated in DMD patients due to muscle damage, and levels of creatine kinase are used for diagnostic and prognostic purposes. This Example demonstrates that laminin-111 therapy resulted in a 2.6-fold reduction in serum creatine kinase levels compared to PBS control (FIG. 34, $*P<0.05$, n=5 mice/group). These levels were not statistically different from creatine kinase levels in wild-type mice. These results demonstrate that laminin-111 protein can be systemically delivered to major muscle systems in mdx mice to prevent dystrophic pathology.

Since the laminin-111 protein is relatively large and could adversely affect renal function, serum creatine and blood urea nitrogen (BUN) were measured. Analysis revealed that creatine and BUN were not statistically different between laminin-111-treated mdx and control mice (FIG. 34, $*P<0.05$, n=5 mice/group). These data indicate laminin-111 protein therapy had no adverse effects on renal function.

This Example demonstrates for the first time that a single systemic dose of laminin-111 protein prevents the onset of muscle disease for at least three-weeks in mice genetically destined to develop muscular dystrophy. Together these findings demonstrate that laminin-111 may be a highly potent, novel protein therapeutic for Duchenne Muscular Dystrophy. In addition, laminin-111 protein therapy may prove effective in the treatment of other muscle diseases including congenital muscular dystrophy type 1A, Limb-Girdle muscular dystrophy and $\alpha 7$ integrin congenital myopathy. The effectiveness of laminin-111 protein injections in dystrophic mice represents a novel paradigm demonstrating that systemic delivery of extracellular matrix proteins could be explored as a therapy for genetic diseases.

It is to be understood that the above discussion provides a detailed description of various embodiments. The above descriptions will enable those skilled in the art to make many departures from the particular examples described above to provide apparatuses constructed in accordance with the present disclosure. The embodiments are illustrative, and not intended to limit the scope of the present disclosure. The scope of the present disclosure is rather to be determined by the scope of the claims as issued and equivalents thereto.

We claim:

1. A method of enhancing muscle regeneration or repair in a subject comprising systemically administering a therapeutically effective amount of laminin-1 to the subject in need thereof.

2. The method of claim 1, further comprising diagnosing the subject with a condition characterized by impaired muscle regeneration prior to administering a therapeutically effective amount of laminin-1 to the subject.

3. The method of claim 1, wherein the subject has a condition characterized by impaired production of a component of the costamere.

4. The method of claim 1, wherein the subject has impaired production of dystrophin.

5. The method of claim 1, wherein the subject has impaired production of laminin.

6. The method of claim 1, wherein the subject has impaired production of $\alpha 7\beta 1$ integrin.

7. The method of claim 1, further comprising administering with the laminin-1 an additional therapeutic agent is selected from a costamere protein, satellite cells, stem cells, and myocytes.

8. The method of claim 1, wherein the laminin is administered in an amount between about 0.01 µg/kg and about 1000 mg/kg of the subject's weight, such as about 0.1 mg/kg and about 1000 mg/kg of the subject's weight or about 0.2 mg/kg and about 2 mg/kg of the subject's weight.

9. The method of claim 1, wherein the subject has Duchenne muscular dystrophy.

10. The method of claim 1, wherein the subject has a congenital muscular dystrophy.

11. The method of claim 1, wherein the congenital muscular dystrophy is merosin deficient congenital muscular dystrophy (MCMD).

12. The method of claim 1, wherein systemically administering comprises systemically administering a single dose of laminin-1 once every week to a subject in need thereof.

13. The method of claim 1, wherein systemically administering comprises intraperitoneal administration.

14. The method of claim 13, wherein intraperitoneal administration comprises intraperitoneally administering a single dose of laminin-1 intraperitoneally once every week to a subject in need thereof.

15. The method of claim 1, wherein systemically administering comprises parenteral administration.

16. The method of claim 15, wherein parenteral administration comprises parenterally administering a single dose of laminin-1 intraperitoneally once every week to a subject in need thereof.

17. A method of promoting wound healing in a subject comprising systemically administering an effective amount of laminin-1 to the subject.

18. A method of enhancing muscle regeneration or repair in a subject comprising systemically administering a therapeutically effective amount of at least a portion of the $\alpha 1$ chain of laminin to the subject in need thereof.

19. The method of claim 18, wherein the subject has Duchenne muscular dystrophy.

20. The method of claim 18, wherein the subject has a congenital muscular dystrophy.

21. The method of claim 18, wherein the congenital muscular dystrophy is merosin deficient congenital muscular dystrophy (MCMD).

22. The method of claim 18, wherein systemically administering comprises systemically administering a single dose of at least a portion of the $\alpha 1$ chain of laminin once every week to a subject in need thereof.

* * * * *